(12) United States Patent
Barr et al.

(10) Patent No.: US 10,501,384 B2
(45) Date of Patent: Dec. 10, 2019

(54) COMPOSITION CONTAINING N-(N-BUTYL) THIOPHOSPHORIC TRIAMIDE ADDUCTS AND REACTION PRODUCTS

(71) Applicant: Koch Agronomic Services, LLC, Wichita, KS (US)

(72) Inventors: Douglas Barr, Decatur, GA (US); Ethel Garnier, Tucker, GA (US); Stanley Freeman, Decatur, GA (US)

(73) Assignee: Koch Agronomic Services, LLC, Wichita, KS (US)

( * ) Notice: Subject to any disclaimer, the term of this patent is extended or adjusted under 35 U.S.C. 154(b) by 0 days.

(21) Appl. No.: 15/875,748

(22) Filed: Jan. 19, 2018

(65) Prior Publication Data

US 2018/0208520 A1 Jul. 26, 2018

Related U.S. Application Data

(60) Provisional application No. 62/448,706, filed on Jan. 20, 2017.

(51) Int. Cl.
*C05G 3/08* (2006.01)
*C05C 9/00* (2006.01)
*C07F 9/22* (2006.01)

(52) U.S. Cl.
CPC ............... *C05G 3/08* (2013.01); *C05C 9/00* (2013.01); *C07F 9/224* (2013.01); *Y02P 60/218* (2015.11)

(58) Field of Classification Search
None
See application file for complete search history.

(56) References Cited

U.S. PATENT DOCUMENTS

| | | | |
|---|---|---|---|
| 1,940,383 A | 12/1933 | Woodstock | |
| 2007/0157689 A1 | 7/2007 | Sutton et al. | |
| 2014/0047884 A1 | 2/2014 | Gabrielson et al. | |
| 2016/0060184 A1* | 3/2016 | Gabrielson | C05G 3/08 71/30 |
| 2017/0137335 A1* | 5/2017 | Barr | C09K 15/26 |

FOREIGN PATENT DOCUMENTS

| | | |
|---|---|---|
| CN | 101045656 A | 10/2007 |
| CN | 104447025 A | 3/2015 |
| DE | 102006015362 A1 | 10/2007 |
| WO | 2008002503 A2 | 1/2008 |
| WO | 2010093462 A1 | 8/2010 |
| WO | 2011137393 A1 | 11/2011 |
| WO | 2013123229 A1 | 8/2013 |
| WO | 2015027244 A1 | 2/2015 |
| WO | 2017019528 A1 | 2/2017 |
| WO | 2017083714 A1 | 5/2017 |

OTHER PUBLICATIONS

International Search Report for corresponding PCT Patent Application No. PCT/IB2018/050367, dated May 1, 2018, 5 pages.

* cited by examiner

*Primary Examiner* — Wayne A Langel

(57) ABSTRACT

Reaction products and methods for making and using such reaction products are provided. For example, a reaction product comprising an adduct formed from two or more of a first nucleophile (e.g., including, but not limited to, a urease inhibitor), a second nucleophile, and an electrophile is described, which can be provided in various forms. Such a reaction product can be in the form of a solid or solution. Such a reaction product can also be combined with one or more additional components, including but not limited to, free urease inhibitor and/or a nitrogen-based fertilizer composition.

27 Claims, 6 Drawing Sheets

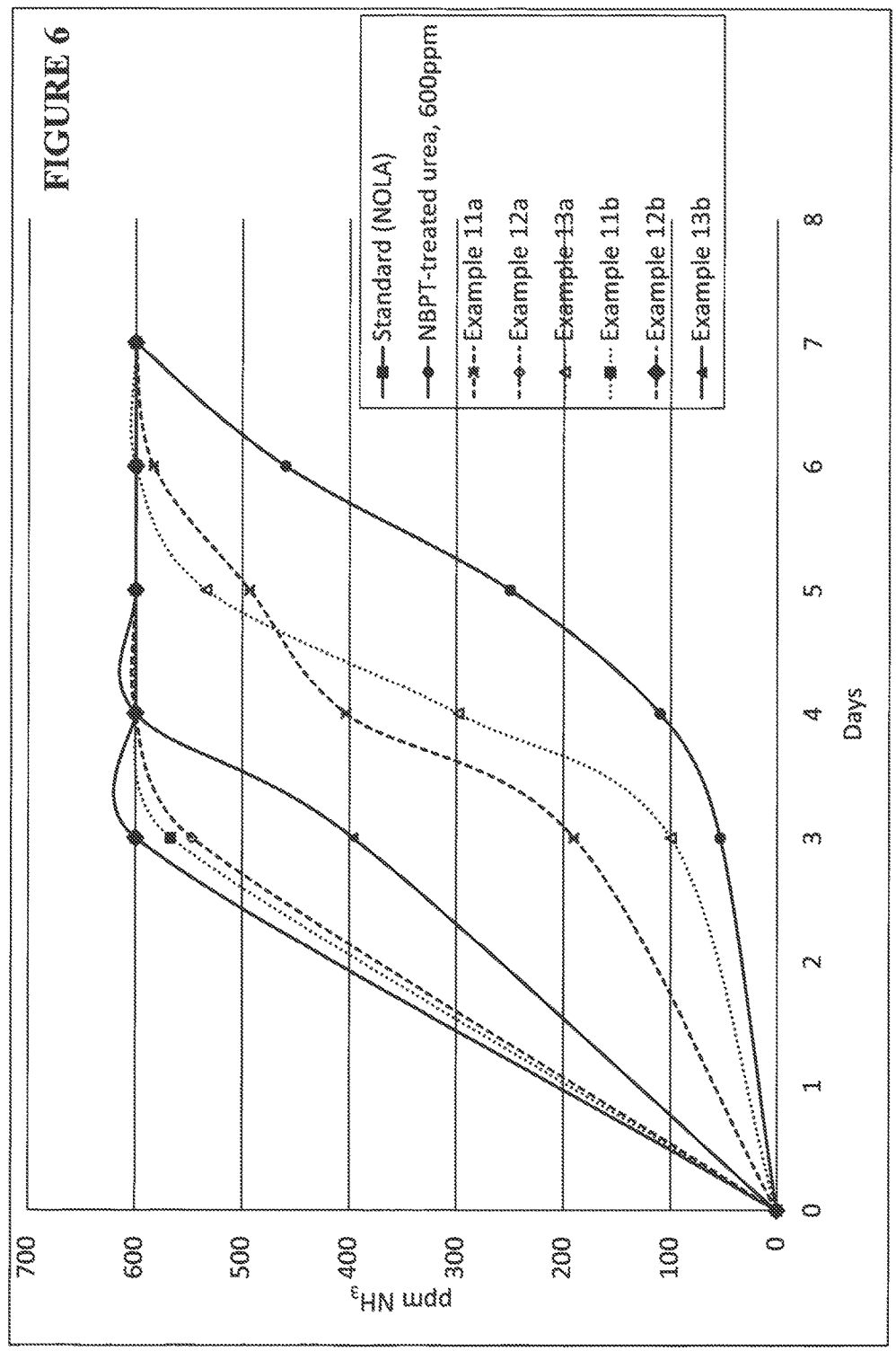

COMPOSITION CONTAINING N-(N-BUTYL) THIOPHOSPHORIC TRIAMIDE ADDUCTS AND REACTION PRODUCTS

CROSS REFERENCE TO RELATED APPLICATIONS

This present application claims priority to U.S. Provisional Patent Application No. 62/448,706 filed Jan. 20, 2017 the disclosures of which are incorporated by reference herein. FIELD OF THE DISCLOSURE The present subject matter relates generally to compositions comprising urease inhibitors, nitrification inhibitors, or both and to methods of preparing and using such compositions.

BACKGROUND

Fertilizers have been used for some time to provide nitrogen to the soil. The most widely used and agriculturally important nitrogen fertilizer is urea, $CO(NH_2)_2$. Most of the urea currently produced is used as a fertilizer in its granular (or prilled) form. After application of urea to soil, it is readily hydrolyzed to yield ammonia and carbon dioxide. This process is catalyzed by the enzyme urease, which is produced by some bacteria and fungi that may be present in the soil. The gaseous products formed by the hydrolysis reaction (i.e., ammonia and carbon dioxide) can volatilize to the atmosphere and thus, substantial losses from the total amount of the nitrogen applied to the soil can and does occur.

Attempts to reduce losses of applied nitrogen have utilized urease inhibitors and/or nitrification inhibitors as additives to the fertilizer. Urease inhibitors are compounds capable of inhibiting the catalytic activity of the urease enzyme on urea in the soil. When incorporated into a urea-containing fertilizer, urease inhibitors can reduce the rate at which urea is hydrolyzed in the soil to ammonia. Nitrification inhibitors are compounds capable of inhibiting the bacterial oxidation of ammonium to nitrate in the soil. Urease inhibitors and nitrification inhibitors can be associated with fertilizers in various ways. For example, they can be coated onto fertilizer granules or mixed into fertilizer matrices. A number of granulation methods are known, including falling curtain, spherudization-agglomeration drum granulation, prilling, and fluid bed granulation technologies.

Although both urease inhibitors and nitrification inhibitors can improve the function of fertilizer by decreasing nitrogen loss, both types of inhibitors suffer from certain disadvantages. The most developed thiophosphoric triamide urease inhibitor (disclosed in U.S. Pat. No. 4,530,714 to Kolc et al., which is incorporated herein by reference) is N-(n-butyl) thiophosphoric triamide (NBPT), which is commercially available for use in agriculture and is marketed in such products as the AGROTAIN® nitrogen stabilizer product line. However, industrial grade NBPT is a solid, waxy compound, and decomposes by the action of water, acid and/or elevated temperature (e.g., believed to degrade at elevated temperatures into compounds that may not provide the desired inhibitory effects on the urease enzyme). Accordingly, its combination with other solid materials to provide a material capable of inhibiting urease, particularly via granulation with urea (which generally employs heat) can be challenging. Nitrification inhibitors tend to leach into the soil, away from the plant, thus becoming ineffective at inhibiting nitrification where it is needed—near the plant.

There is a need, therefore, for improved fertilizers that provide effective urease inhibition and/or effective nitrification inhibition and methods for making and using the same. Further, there is a need for urease inhibitor-containing and/or nitrification inhibitor-containing compositions that can be combined with urea, desirably using current urea manufacturing practices, so as to produce fertilizer compositions that provide effective urease inhibition and/or effective nitrification inhibition.

SUMMARY OF THE INVENTION

As disclosed herein, compositions comprising urease inhibitors and/or nitrification inhibitors and methods for making such compositions are provided. Such compositions generally comprise a reaction product between a first nucleophile, a second nucleophile, and an electrophile (e.g., an aldehyde). Such reaction products can be characterized as adducts, as the products arising from the reaction retain at least portions of two or more of the reactants (i.e., first nucleophile, second nucleophile, and/or electrophile).

Advantageously, one or more of the reactants is an agriculturally beneficial component, e.g., a urease inhibitor or a nitrification inhibitor. Compositions arising from such reactions, comprising the disclosed reaction products, can be provided independently and can, in certain embodiments, be combined with other components. For example, such adduct-containing compositions can be combined with fertilizer materials comprising nitrogen sources, including but not limited to, urea, ammonia, ammonium nitrate, and combinations thereof. Advantageously, adduct-containing compositions disclosed herein, alone or in combination with one or more nitrogen sources, can provide fertilizers that exhibit substantial urease inhibitory effects and can thus be characterized by low ammonia volatilization losses in use (i.e., upon application to soil) and/or can exhibit substantial nitrification inhibition effects.

In one aspect of the disclosure, a composition is provided, comprising an adduct of two or more of N-(n-butyl)thiophosphoric triamide (NBPT), a nucleophile, and an aldehyde. Such adducts can, in some embodiments, be adducts of NBPT and the nucleophile, adducts of NBPT and the aldehyde, adducts of the nucleophile and the aldehyde, or adducts of NBPT, the nucleophile, and the aldehyde. In some embodiments, adducts can comprise two or more equivalents of a given component (or components). For example, in certain embodiments, adducts are provided which comprise two NBPT portions (in combination with a nucleophile portion and/or an aldehyde portion), as will be detailed more fully herein below.

The nucleophile in the disclosed compositions and methods can vary and can be, for example, urea or a nitrification inhibitor. Certain exemplary nitrification inhibitors include, but are not limited to, nitrification inhibitors selected from the group consisting of 2-chloro-6-trichloromethyl-pyridine, 5-ethoxy-3-trichloromethyl-1,2,4-thiadiazol, dicyandiamide, 2-amino-4-chloro-6-methyl-pyrimidine, 1,3-benzothiazole-2-thiol, 4-amino-N-1,3-thiazol-2-ylbenzenesulfonamide, thiourea, guanidine, 3,4-dimethylpyrazole phosphate, 3,5-dimethylpyrazole, 2,4-diamino-6-trichloromethyl-5-triazine, polyetherionophores, 4-amino-1,2,4-triazole, 3-mercapto-1,2,4-triazole, potassium azide, carbon bisulfide, sodium trithiocarbonate, ammonium dithiocarbamate, 2,3, dihydro-2,2-dimethyl-7-benzofuranol methylcarbamate, N-(2,6-dimethylphenyl)-N-(methoxyacetyl)-alanine methyl ester, ammonium thiosulfate, 1-hydroxypyrazole, 2-methylpyrazole-1-carboxamide, and combinations thereof. In particular embodiments, the nucleophile is a nitrification inhibitor selected from the group consisting of dicyandiamide, thiourea, 4-amino-1,2, 4-triazole, 3,5-dimethylpyrazole, and combinations thereof.

The aldehyde can similarly vary in the compositions and methods disclosed herein. For example, in some embodiments, the aldehyde is selected from the group consisting of formaldehyde, acetaldehyde, propionaldehyde, butyraldehyde, isobutyraldehyde, 2-methyl butanal, 2-ethyl butanal, pentanal, benzaldehyde, furfural, glyoxal, malondialdehyde, succindialdehyde, glutaraldehyde, and combinations thereof.

Various adduct structures are encompassed within the present disclosure. In one embodiment, a composition is provided comprising an adduct of the following formula:

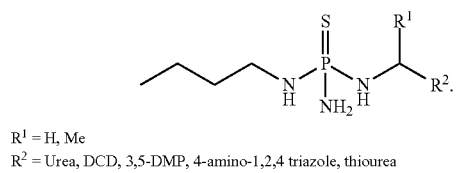

$R^1$ = H, Me
$R^2$ = Urea, DCD, 3,5-DMP, 4-amino-1,2,4 triazole, thiourea

In one embodiment, a composition is provided comprising an adduct of the following formula:

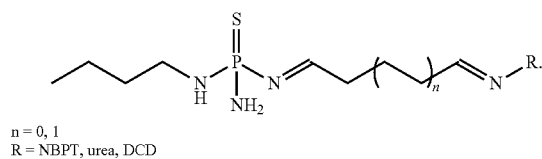

n = 0, 1
R = NBPT, urea, DCD

The compositions disclosed herein can include a range of other components and materials. For example, certain compositions further comprise one or more materials selected from the group consisting of free NBPT, free formaldehyde, urea, urea formaldehyde polymer (UFP), water, and combinations thereof. The compositions can, in various embodiments, be in the form of a solution, e.g., a solution comprising the adduct or adducts in an organic solvent. The compositions can, in some embodiments, be a synergistic mixture of free NBPT and the adduct.

The disclosure further provides, in some aspects, fertilizer compositions comprising urea and the adduct-containing compositions generally disclosed herein. Such fertilizer compositions in some embodiments comprise about 90% by weight or more urea, about 98% by weight or more urea, or about 99% by weight or more urea.

In another aspect, the disclosure provides a method of forming a fertilizer composition, the method comprising combining a fertilizer material with an adduct-containing composition as described herein. The adduct-containing composition can, in certain embodiments, be used in the form of a solution comprising the adduct in an organic solvent. In some embodiments, the method further comprises combining free NBPT with one or both of the fertilizer material and the adduct-containing composition. The disclosure further describes methods of using such fertilizer compositions, e.g., providing a method of fertilizing soil, comprising applying the adduct-containing compositions disclosed herein (including, in some embodiments, fertilizer compositions comprising such adduct-containing compositions) to the soil.

The disclosure also provides a method of making a urease inhibiting composition, the method comprising combining a N-(n-butyl)thiophosphoric triamide (NBPT), a nucleophile, and an aldehyde to form an adduct of NBPT with one or both of the nucleophile and the aldehyde.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

FIG. 6 is a graph of ammonia ($NH_3$) volatilization from soil samples to which further various treated ureas have been added (urea treated with NBPT-adduct containing composition and urea treated with both free NBPT and NBPT adduct-containing compositions).

DETAILED DESCRIPTION OF THE INVENTION

Figure 1:
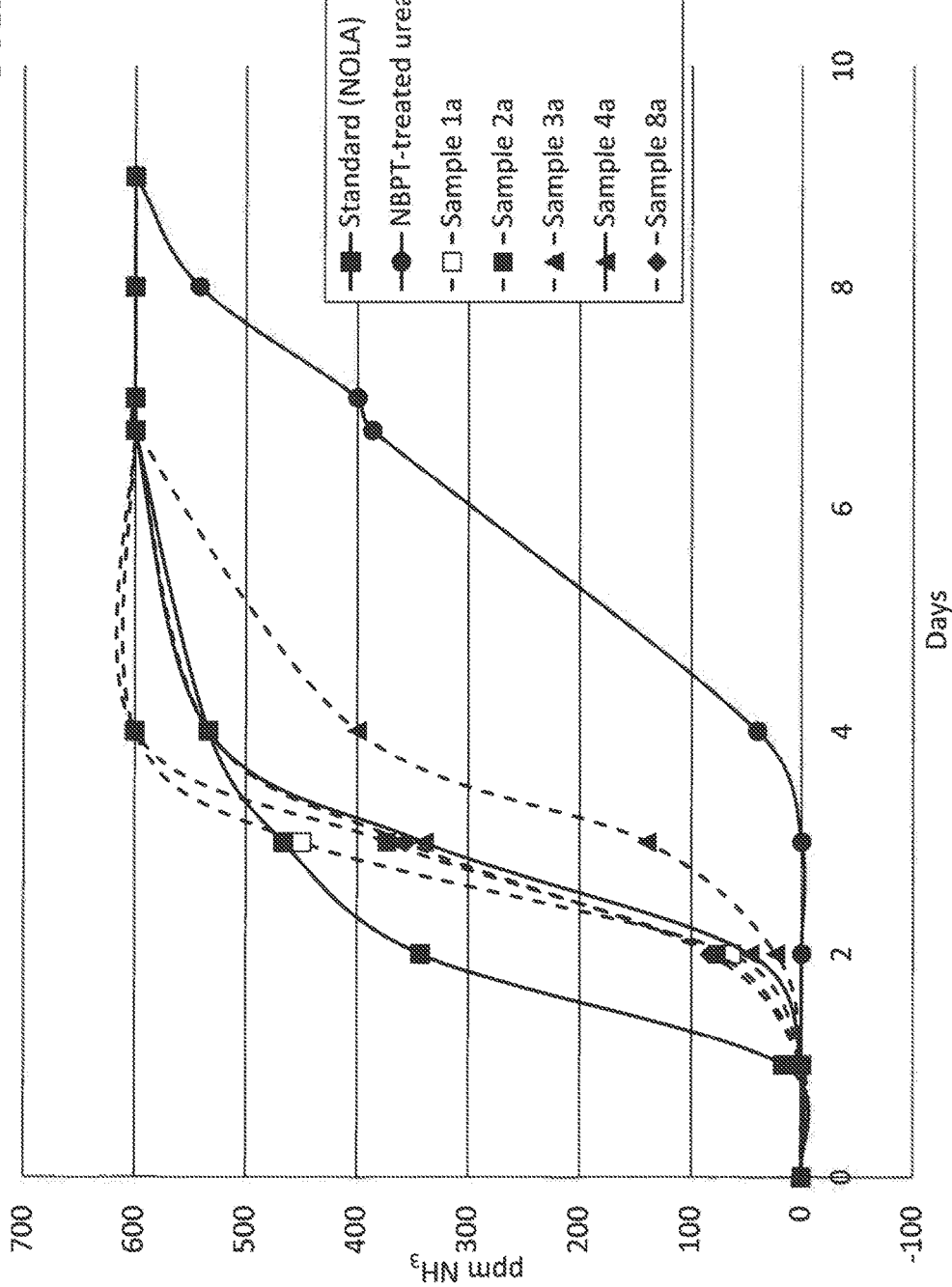
FIG. 1 is a graph of ammonia ($NH_3$) volatilization from soil samples to which various treated ureas have been added (urea treated with NBPT adduct-containing compositions)

It is noted here that as used in this specification and the appended claims, the singular forms "a," "an," and "the" include plural reference unless the context clearly dictates otherwise. All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt. %" herein. All molecular weights as used herein are weight average molecular weights expressed as grams/mole, unless otherwise specified.

According to the present disclosure, compositions exhibiting effective urease inhibition and methods of producing such compositions are provided. It was surprisingly found that, as higher amounts of urease inhibitor were added to mixtures of urea and formaldehyde, the amount of free urease inhibitor present in the final product mixture did not scale accordingly. Subsequently, it was determined that at least a portion of the urease inhibitor added to the urea and formaldehyde was reacting under the conditions to which it was subjected to form an adduct comprising the urease inhibitor (thus decreasing the concentration of free urease inhibitor in the final product mixture). See U.S. patent application Ser. No. 15/349,512, filed Nov. 11, 2016, which is incorporated by reference herein in its entirety.

It has since been found that a range of other compositions, generally comprising a reaction product arising from reaction of a first nucleophile comprising a urease inhibitor, a second nucleophile (e.g., a nitrification inhibitor or urea), and an electrophile (e.g. an aldehyde) can be prepared which, in some embodiments, surprisingly exhibits enhanced agricultural effects, e.g., enhanced urease inhibition and/or enhanced nitrification inhibition. It is noted that in the present application, the designations of certain reactants as "first" and "second" nucleophiles are arbitrary, and are intended only to refer to different specific compounds used to produce reaction products as disclosed herein.

Urease inhibitor-containing reaction products (and/or adducts isolated therefrom) can, in some embodiments, exhibit synergistic urease inhibition in combination with additional urease inhibitor. The reaction products disclosed herein can be provided as-formed, can be purified to isolate one or more components (e.g., adducts) therefrom, or can be provided in combination with one or more other components, such as additional urease inhibitor, nitrification inhibitor, and/or a fertilizer composition, e.g., in the form of a nitrogen source including, but not limited to, a urea source. The compositions disclosed herein can, in some embodiments, exhibit novel slow release of the one or more urease inhibitors.

First Nucleophile (Reactant)

As referenced, the "first nucleophile" component used in preparing reaction products comprising adducts as generally disclosed herein can be selected from various compounds. In preferred embodiments, the first nucleophile has agricultural significance, e.g., it is a compound known to function as a urease inhibitor.

As used herein, the term "urease inhibitor" refers to any compound that reduces, inhibits, or otherwise slows down the conversion of urea to ammonium ($NH_4^+$) in soil. Exemplary urease inhibitors include thiophosphoric triamides and phosphoric triamides of the general formula (1):

$$X=P(NH_2)_2NR^1R^2 \quad \text{(FORMULA 1)}$$

where X=oxygen or sulfur, and $R^1$ and $R^2$ are independently selected from hydrogen, $C_1$-$C_{12}$ alkyl, $C_3$-$C_{12}$ cycloalkyl, $C_6$-$C_{14}$ aryl, $C_2$-$C_{12}$ alkenyl, $C_2$-$C_{12}$ alkynyl, $C_5$-$C_{14}$ heteroaryl, heteroalkyl, $C_2$-$C_{14}$ heteroalkenyl, $C_2$-$C_{14}$ heteroalkynyl, or $C_3$-$C_{12}$ cycloheteroalkyl groups.

In certain embodiments, urease inhibitors are N-(alkyl) thiophosphoric triamide urease inhibitors as described in U.S. Pat. No. 4,530,714 to Kolc et al., which is incorporated herein by reference. Particular illustrative urease inhibitors can include, but are not limited to, N-(n-butyl)thiophosphoric triamide, N-(n-butyl)phosphoric triamide, thiophosphoryl triamide, phenyl phosphorodiamidate, cyclohexyl phosphoric triamide, cyclohexyl thiophosphoric triamide, phosphoric triamide, hydroquinone, p-benzoquinone, hexamidocyclotriphosphazene, thiopyridines, thiopyrimidines, thiopyridine-N-oxides, N,N-dihalo-2-imidazolidinone, N-halo-2-oxazolidinone, derivatives thereof, or any combination thereof. Other examples of urease inhibitors include phenylphosphorodiamidate (PPD/PPDA), hydroquinone, N-(2-nitrophenyl) phosphoric acid triamide (2-NPT), ammonium thiosulphate (ATS) and organo-phosphorous analogs of urea, which are effective inhibitors of urease activity (see e.g. Kiss and Simihaian, Improving Efficiency of Urea Fertilizers by Inhibition of Soil Urease Activity. Kluwer Academic Publishers, Dordrecht, The Netherlands, 2002; Watson, Urease inhibitors. IFA International Workshop on Enhanced-Efficiency Fertilizers, Frankfurt. International Fertilizer Industry Association, Paris, France 2005).

In particular embodiments, the urease inhibitor can be or can include N-(n-butyl) thiophosphoric triamide (NBPT). The preparation of phosphoramide urease inhibitors such as NBPT can be accomplished, for example, by known methods starting from thiophosphoryl chloride, primary or secondary amines and ammonia, as described, for example, in U.S. Pat. No. 5,770,771, which is incorporated herein by reference. In a first step, thiophosphoryl chloride is reacted with one equivalent of a primary or secondary amine in the presence of a base, and the product is subsequently reacted with an excess of ammonia to give the end product. Other methods include those described in U.S. Pat. No. 8,075,659, which is incorporated herein by reference, where thiophosphoryl chloride is reacted with a primary and/or secondary amine and subsequently with ammonia. However this method can result in mixtures. Accordingly, when N-(n-butyl)thiophosphoric triamide (NBPT) or other urease inhibitors are used, it should be understood that this refers not only to the urease inhibitor in its pure form, but also to various commercial/industrial grades of the compound, which can contain up to 50 percent (or less), preferably not more than 20 percent, of impurities, depending on the method of synthesis and purification scheme(s), if any, employed in the production thereof. Combinations of urease inhibitors, for example using mixtures of NBPT and other alkyl-substituted thiophosphoric triamides, are known.

Representative grades of urease inhibitor may contain up to about 50 wt. %, about 40% about 30%, about 20% about 19 wt. %, about 18 wt. %, about 17 wt. %, about 16 wt. %, about 15 wt. %, about 14 wt. %, about 13 wt. %, about 12 wt. %, about 11 wt. %, 10 wt. %, about 9 wt. %, about 8 wt. %, about 7 wt. %, about 6 wt. % about 5 wt. %, about 4 wt. %, about 3 wt. %, about 2 wt. %, or about 1 wt. % impurities, depending on the method of synthesis and purification scheme(s), if any, employed in the production of the urease inhibitor. A typical impurity in NBPT is $PO(NH_2)_3$ which can catalyze the decomposition of NBPT under aqueous conditions. Thus in some embodiments, the urease inhibitor used is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% pure.

Certain urease inhibitor-containing adducts are disclosed in U.S. patent application Ser. No. 15/217,195 to Barr et al., filed Jul. 22, 2016, which is incorporated herein by reference in its entirety. For simplicity, certain urease inhibitor-containing compositions and methods provided herein may be described in relation to embodiments wherein NBPT is the urease inhibitor. Description of the invention in terms wherein NBPT is the urease inhibitor should not be viewed as necessarily excluding the use of other urease inhibitors, or combinations of urease inhibitors, unless expressly noted.

Second Nucleophile (Reactant)

The second nucleophile employed in producing the reaction products (and thus present in certain adducts provided according to the disclosure) can vary. Advantageously, in some embodiments, the second nucleophile is a common component of fertilizer compositions. For example, in some embodiments, the second nucleophile is urea or a nitrification inhibitor.

As used herein, the term "nitrification inhibitor" refers to any compound(s) that reduces, inhibits, or otherwise slows down the conversion of ammonium ($NH_4^+$) to nitrate in soil when present as compared to the conversion of ammonium ($NH_4^+$) to nitrate in soil when not present. Examples of nitrification inhibitors include, but are not limited to, 2-chloro-6-trichloromethyl-pyridine, 5-ethoxy-3-trichloromethyl-1,2,4-thiadiazol, dicyandiamide (DCD), 2-amino-4-chloro-6-methyl-pyrimidine, 1,3-benzothiazole-2-thiol, 4-amino-N-1,3-thiazol-2-ylbenzenesulfonamide, thiourea, guanidine, 3,4-dimethylpyrazole phosphate (DMPP), 3,5-dimethylpyrazole (DMP), 2,4-diamino-6-trichloromethyl-5-triazine, polyetherionophores, 4-amino-1,2,4-triazole, 3-mercapto-1,2,4-triazole, potassium azide, carbon bisulfide, sodium trithiocarbonate, ammonium dithiocarbamate, 2,3, dihydro-2,2-dimethyl-7-benzofuranol methyl-carbamate, N-(2,6-dimethylphenyl)-N-(methoxyacetyl)-alanine methyl ester, ammonium thiosulfate, 1-hydroxypyrazole, 2-methylpyrazole-1-carboxamide, derivatives thereof, and any combination thereof. In at least one example, a nitrification inhibitor can be or include dicyandiamide (DCD). Certain nitrification inhibitor-containing adducts are disclosed in U.S. Pat. No. 9,440,890 to Gabrielson et al., which is incorporated herein by reference in its entirety. Certain specific nitrification inhibitors are dicyandiamide (DCD), 4-amino-1,2,4-triazole (AT, ATC), thiourea, and 3,5-dimethylpyrazole (DMP).

Where the second nucleophile comprises urea, urea can be provided in various forms. For example, the urea can be a solid in the form of prills, flakes, granules, and the like, and/or a solution, such as an aqueous solution, and/or in the form of molten urea. At least a portion of the urea can be in the form of animal waste. Both urea and combined urea-formaldehyde products can be used according to the present disclosure. Illustrative urea-formaldehyde products can include, but are not limited to, urea-formaldehyde concentrate ("UFC") and urea-formaldehyde polymers ("UFP"). These types of products can be as discussed and described in U.S. Pat. Nos. 5,362,842 and 5,389,716 to Graves et al., for example, which are incorporated herein by reference. Any form of urea or urea in combination with formaldehyde can be used to make a UFP. Examples of solid UFP include PERGOPAK M® 2, available from Albemarle Corporation and NITAMIN 36S, available from Koch Agronomic Services, LLC. Any of these urea sources can be used alone or in any combination to prepare the reaction products disclosed herein.

Electrophile (Reactant)

The electrophile employed in producing the reaction products (and thus present in certain adducts provided according to the disclosure) can be, but is not limited to, an aldehyde. Aldehydes are compounds with the structure of Formula 2:

(FORMULA 2)

wherein R can be, e.g., H, a substituted or unsubstituted alkyl group, a substituted or unsubstituted alkenyl group, a substituted or unsubstituted alkynyl group, a substituted or unsubstituted heteroalkyl group, a substituted or unsubstituted aryl, or a substituted or unsubstituted heteroaryl.

Alkyl refers to an alkane chemical moiety, and can be linear, branched, or cyclic. Lower alkyl groups can comprise from 1-6 carbon atoms and higher alkyl groups can include 7-20 carbon atoms. Examples of such moieties include, but are not limited to, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, cyclopropyl, cyclobutyl, and cyclopentyl. Alkenyl refers to a moiety containing carbon and hydrogen with at least one double bond and can be linear, branched, or cyclic. Examples of alkenyl moieties include, but are not limited to, $CH=CH_2$, $CH=CHCH_3$, $CH_2CH=CH$, $CH=CHCH_2CH_3$, $CH_2CH=CHCH_3$, $CH_2CH_2CH=CH_2$, $CH=CHCH_2CH_2CH_3$, $CH=CHCH(CH_3)_2$, cyclopentenyl, and cyclohexenyl. Alkynyl refers to a moiety containing carbon and hydrogen and includes a triple bond and can be linear or branched. Alkynyl groups include, but are not limited to, CCH, $CCCH_3$, $CH_2CCH$, $CCCH_2CH_3$, $CH_2CCCH_3$, $CH_2CH_2CCH_3$, $CCCH_2CH_2CH_3$, etc. Heteroalkyl refers to an alkyl group wherein at least one of the carbon atoms is replaced with a heteroatom (e.g., oxygen, nitrogen, or sulfur). Aryl refers to an aromatic group containing only carbon and hydrogen (e.g., $C_6H_5$ ("aryl"), and $C_{10}H_8$). Heteroaryl refers to an aromatic group wherein at least one of the carbon atoms is replaced with a heteroatom (e.g., oxygen, nitrogen, or sulfur). Examples of such moieties include, but are not limited to, $C_4H_4O$ (furan), $C_4H_4NH$ (pyrrole), $C_3N_2H_4$ (imidazole), $C_4H_2S$, and $C_5H_4N$. "Substituted," as used herein refers to moieties wherein one or more hydrogen atom is replaced with another chemical group, including, but not limited to, a halo (Cl, F, I, or Br), OH, alkyl, alkoxy (O-alkyl), $CF_3$, $OCF_3$, $NH_2$, NHR, and the like.

Aldehydes as referred to herein include dialdehydes, e.g., as represented by Formula 3, below, wherein R is selected from relevant R groups referenced herein above, suitably modified so as to be difunctional (to attach to both carbonyl groups of the dialdehyde).

(FORMULA 3)

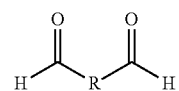

Certain exemplary aldehydes used according to the compositions and methods disclosed herein include, but are not limited to, formaldehyde (Formula 2, R=H), acetaldehyde (Formula 2, R=$CH_3$), propionaldehyde, butyraldehyde, isobutyraldehyde, 2-methyl butanal, 2-ethyl butanal, pentanal, benzaldehyde, furfural, glyoxal, malondialdehyde, succindialdehyde, glutaraldehyde, and analogues thereof.

It is noted that, where the aldehyde comprises formaldehyde, the formaldehyde can be provided in combination with other components, e.g., in combination with urea where the second nucleophile comprises urea (e.g., in the form of a mixture or polymer with urea). In such embodiments, additional formaldehyde need not be added to form the desired adduct, although the disclosure is not limited thereto and it is possible to add additional formaldehyde to such urea-formaldehyde products. Accordingly, although formaldehyde is described herein as a separate, independent reagent to produce adducts provided according to the present disclosure, it is noted that in certain embodiments, formaldehyde that is incorporated within the adduct is already present within the urea source (i.e., formaldehyde is not intentionally added to the reaction). In some embodiments, formaldehyde is intentionally added as a reagent to prepare the reaction products disclosed herein, and the formaldehyde can be in various forms. For example, paraform (solid, polymerized formaldehyde) and/or formalin solutions (aqueous solutions of formaldehyde, sometimes with methanol, in about 10 wt. %, about 20 wt. %, about 37 wt. %, about 40 wt. %, or about 50 wt. %, based on the weight of the formalin solution) are commonly used forms of formaldehyde. In some embodiments, the formaldehyde can be an aqueous solution having a concentration of formaldehyde ranging from about 10 wt. % to about 50 wt. % based on total weight of the aqueous solution. Formaldehyde gas can also be used. Formaldehyde substituted in part or in whole with substituted aldehydes such as acetaldehyde and/or propylaldehyde can also be used as the source of formaldehyde. Any of these forms of formaldehyde sources can be used alone or in any combination to prepare the reaction product described herein.

Reaction Products Comprising Adducts

As noted herein, the three components referenced above are combined so as to form one or more adducts, wherein an adduct is understood to retain at least portions of two or more of the reactants (i.e., first nucleophile, second nucleophile, and/or electrophile). The reaction products provided according to the methods disclosed hereinabove can comprise one or a plurality of structurally different adducts. For example, a given reaction product can comprise at least one adduct, at least two different adducts, at least three different adducts, at least four different adducts, at least five different adducts, at least ten different adducts, at least twenty-five different adducts, at least about fifty different adducts, or at least about one hundred different adducts. The adducts may be in the form of discrete compounds, oligomers, polymers, and combinations thereof. The overall amount of adduct formed can vary and, likewise, the amount of each different adduct (where more than one adduct is present in the composition) can vary.

In certain embodiments, reaction products are provided that comprise one or more adducts formed from two or more of a urease inhibitor (e.g., NBPT), a second nucleophile, and an electrophile comprising an aldehyde. Certain such non-limiting, exemplary adducts can be represented as follows:

(FORMULA 4)

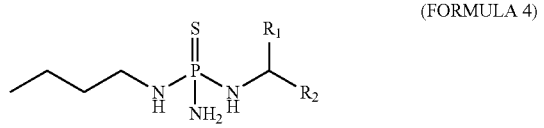

wherein $R_1$ represents a component of the aldehyde (i.e., the "R" group from Formula 2 above) and $R_2$ represents a component of the second nucleophile. As shown, the structure of Formula 4 can be viewed as incorporating components from all three reactants disclosed herein (i.e., the first nucleophile, second nucleophile, and electrophile).

For example, in one specific embodiment, where the first nucleophile is NBPT, the second nucleophile is DCD, and the aldehyde is formaldehyde, the reaction product can comprise an adduct according to the following formula:

(FORMULA 4A)

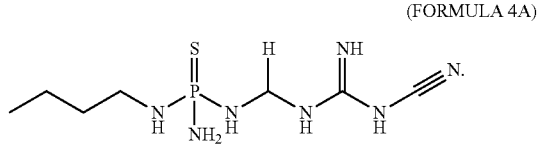 [SMILES: CCCCNP(N)(=S)NCNC(=N)NC#N]

In another specific embodiment, wherein the first nucleophile is NBPT, the second nucleophile is 4-amino-1,2,4-triazole, and the aldehyde is acetaldehyde, the reaction product can comprise an adduct according to the following formula:

(FORMULA 4B)

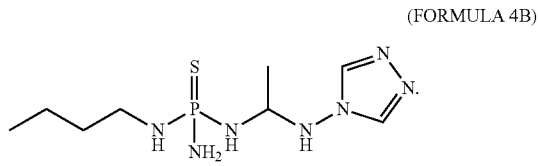 [SMILES: CCCCNP(N)(=S)NC(C)Nn1cnnc1]

In another embodiment, the first nucleophile is 3,5-DMP and an adduct is provided according to the following structure:

(FORMULA 5)

It is generally understood that, under certain reaction conditions, various adducts can be formed, depending upon, e.g., the reactants, the reaction conditions. In some embodiments, a combination of components (e.g., urease inhibitor, second nucleophile, and aldehyde) leads to only one adduct and in other embodiments, a combination of components leads to a mixture of two or more structurally different adducts. In some embodiments, adducts are provided which do not include contributions from one or more of the reactants.

In some embodiments, adducts may be formed which contain two or more portions of a single reactant type (e.g., two portions from the first nucleophile structure, two portions from the second nucleophile structure, or two portions of the electrophile structure). For example, an adduct may be provided according to Formula 6:

(FORMULA 6)

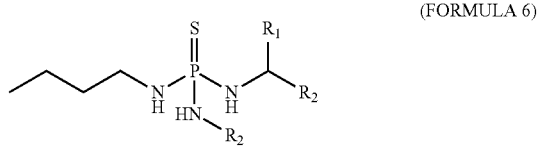

In further embodiments, e.g., where a dialdehyde is used as the electrophile, certain adducts can be formed that have the general structure of Formula 7:

(FORMULA 7)

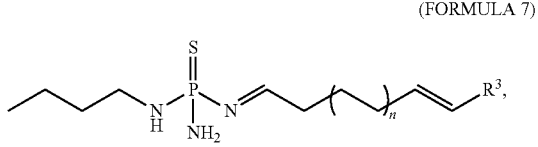

wherein n is 0 or 1 and $R^3$ is one of the nucleophilic reactants (i.e., the first nucleophile or the second nucleophile), e.g., including, but not limited to, NBPT, urea, or DCD.

It is understood that the structures herein above are not intended to be limiting. A range of other adducts can be provided, in addition or in the alternative to those referenced herein above. The specific adduct or adducts formed can depend, in various embodiments, on the specific reactants, their amounts, and/or on the method by which the reaction product is prepared (e.g., the specific conditions of reaction).

Method of Preparing Reaction Products Comprising Adducts

The method of preparing the reaction product disclosed herein can vary. Generally, the first nucleophile is combined with, mixed, or otherwise contacted with the second nucleophile and the electrophile. Accordingly, in some embodiments, the disclosure provides a method for making an adduct, comprising combining a first nucleophile, a second nucleophile, and an electrophile such that at least one adduct is formed. For example, at least a portion of the first nucleophile (e.g., urease inhibitor) can react with at least a portion of the second nucleophile and/or at least a portion of the electrophile to form one or more structurally different adducts (including, but not limited to, the structures represented above).

The reactants (i.e., first and second nucleophiles and electrophile) can be combined with one another in any order or sequence. For example, in one embodiment, the first and second nucleophile are combined and the electrophile is added thereto. In another embodiment, the first nucleophile is combined with the electrophile and the second nucleophile is added thereto or the second nucleophile is combined with the electrophile and the first nucleophile is added thereto. Additionally, in certain embodiments, other components can be included at any of these stages, alone, or in combination with the first nucleophile, second nucleophile, and/or electrophile.

In these various embodiments, the form of the various reactants involved in adduct formation can vary. For example, the reactants can be used in solid or molten liquid form, in solution form, in suspension/dispersion form, or in the form of a solid material impregnated with the reactant. Where solvents are used at any stage of the combining process, the solvents employed are generally those sufficient to solubilize one or more of the nucleophiles and/or electrophile, and such solvents can include, but are not limited to, aqueous solvents and organic solvents. Suitable solvents can include, for example, water (including aqueous buffers), N-alkyl 2-pyrrolidones (e.g., N-methyl 2-pyrrolidone), glycols and glycol derivatives, ethyl acetate, acetonitrile, propylene glycol, benzyl alcohol, and combinations thereof. Representative solvents known to solubilize NBPT include, but are not limited to, those solvents described in U.S. Pat. Nos. 5,352,265 and 5,364,438 to Weston, U.S. Pat. No. 5,698,003 to Omilinsky et al., U.S. Pat. Nos. 8,048,189 and 8,888,886 to Whitehurst et al., WO2014/100561 to Ortiz-Suarez et al., WO2014/055132 to McNight et al., WO2014/028775 and WO2014/028767 to Gabrielson et al., and EP2032589 to Cigler, which are incorporated herein by reference. In certain embodiments, the solvent, or mixture of solvents, employed to combine the components can be selected from the group consisting of water (including buffered solutions, e.g., phosphate buffered solutions), glycols (e.g., propylene glycol), glycol derivatives and protected glycols (e.g., glycerol including protected glycerols such as isopropylidine glycerol, glycol ethers e.g. monoalkyl glycol ethers, dialkyl glycol ethers), acetonitrile, DMSO, alkanolamines (e.g., triethanolamine, diethanolamine, monoethanolamine, alkyldiethanolamines, dialkylmonoethanolamines, wherein the alkyl group can consist of methyl, ethyl, propyl, or any branched or unbranched alkyl chain), alkylsulfones (e.g., sulfolane), alkyl amides (e.g., N-methyl 2-pyrrolidone, N-ethyl 2-pyrrolidone, N,N-dimethylformamide, or any non-cyclic amide), monoalcohols (e.g., methanol, ethanol, propanol, isopropanol, benzyl alcohol), dibasic esters and derivatives thereof, alkylene carbonates (e.g., ethylene carbonate, propylene carbonate), monobasic esters (e.g., ethyl lactate, ethyl acetate), carboxylic acids (e.g., maleic acid, oleic acid, itaconic acid, acrylic acid, methacrylic acid), glycol esters, and/or surfactants (e.g., alkylbenzenesulfonates, lignin sulfonates, alkylphenol ethoxylates, polyalkoxylated amines) and combinations thereof. Further co-solvents, including but not limited to, liquid amides, 2-pyrrolidone, N-alkyl 2-pyrrolidones, and non-ionic surfactants (e.g., alkylaryl polyether alcohols) can be used in certain embodiments.

Various other additives that do not negatively impact the formation of the adducts disclosed herein can be included in the reaction mixture (i.e., in addition to the first nucleophile, second nucleophile, electrophile, and optional solvent(s)). For example, components (e.g., impurities) that are generally present in one or more of the reactants (e.g., urea or NBPT) are commonly incorporated in the reaction mixture. In some embodiments, components that are desirably included in the final product can be incorporated into the reaction mixture (e.g., dyes, as described in further detail below).

In certain embodiments, monoammonium phosphate (MAP), diammonium phosphate (DAP), and/or ammonium sulfate (AMS) can be used to promote the formation of adducts. Although not intended to be limiting, it is believed that MAP, DAP, or AMS can function as catalysts to facilitate the formation of the adducts disclosed herein. In some embodiments, it may be possible, by including MAP, DAP, and/or AMS (and/or other catalysts), to reduce the reaction time and/or to conduct the reaction at lower temperatures than would otherwise be required to form the adducts. In some embodiments, the use of a particular catalyst may have an effect on the amount and/or type(s) of various adducts formed during the reaction.

Adduct formation can be conducted at various pH values, and in some embodiments, it may be desirable to adjust the pH of the reaction mixture (e.g., by adding acid and/or base). Representative acids include, but are not limited to, solutions of mineral acids such as hydrochloric acid, sulfuric acid, nitric acid, phosphoric acid, and combinations thereof. Exemplary bases include, but are not limited to, solutions of ammonia, amines (e.g., primary, secondary and tertiary amines and polyamines), sodium hydroxide, potassium hydroxide, and combinations thereof. In some embodiments, it may be desirable to employ a buffer solution to control the pH of the reaction mixture. Representative buffer solutions include, but are not limited to, solutions of triethanolamine, sodium borate, potassium bicarbonate, sodium carbonate, and combinations thereof.

The conditions under which the first nucleophile, second nucleophile, and electrophile (and optionally, other additives) are combined can vary. For example, the reaction can be conducted at various temperatures, e.g., ranging from ambient temperature (about 25° C.) to elevated temperatures (above 25° C.). In certain embodiments, the temperature at which the reaction is conducted is at least about 50° C., at least about 60° C., at least about 70° C., at least about 80° C., at least about 90° C., or at least about 100° C., such as about 20° C. to about 150° C., about 50° C. to about 150° C., about 70° C. to about 145° C., about 80° C. to about 140° C., about 90° C. to about 135° C., or about 100° C. to about 130° C.

Advantageously, in some embodiments, the reaction product can be prepared under conditions of conventional urea manufacturing (as described, for example, in Jozeef Meesen, Ullman's Encyclopedia of Industrial Chemistry (2012), vol. 37, pages 657-695, which is incorporated herein by reference), e.g., where urea serves as the second nucleophile. Such urea manufacturing conditions generally include temperatures at which urea is in molten form, e.g., temperatures that are at approximately the melting point of urea (about 130° C. to about 135° C.) or greater. For example, in such embodiments, the other reactants can be added to a molten mixture of urea, which can optionally include formaldehyde or another aldehyde (or a mixture of urea and urea-formaldehyde (i.e., UF, UFC or UFP)). Thus, the reaction product can be formed prior to injection into the molten urea stream. In some such embodiments, unreacted reactants may still be present when the mixture enters the molten urea stream, and further reaction products may form as the mixture combines with the molten urea. The molten urea stream with the reaction products combined therein can then be cooled. For example, the composition can be cooled by subjecting the reaction mixture to typical urea pastillation, prilling or granulation processes (e.g., fluidized bed granulation, drum granulation, sprouted bed granulation, and the like), which generally comprise a cooling step following formation of pastilles, prills and/or granules. Generally, the drying process provides the reaction product in the form of a solid material (e.g., a pastillated, granular or prilled solid).

The first and second nucleophiles and the electrophile (i.e., the reaction mixture) can be maintained together under the reaction conditions for various periods of time. For example, in some embodiments, the reaction can be conducted within a relatively short period (e.g., on the order of minutes, e.g., about 30 seconds to about 30 minutes, about 1 to about 20 minutes, or about 1 to about 10 minutes. In some embodiments, the reaction may be conducted for about 1 minute or longer, about 2 minutes or longer, about 5 minutes or longer, about 10 minutes or longer, about 15 minutes or longer, or about 20 minutes or longer. In certain embodiments, the reaction can be conducted for about 2 hours or less, about 1 hour or less, about 30 minutes or less, about 25 minutes or less, about 20 minutes or less, about 15 minutes or less, or about 10 minutes or less. In some embodiments, the components can be reacted together for a somewhat longer period, e.g., for a period of about 2 hours or longer, about 4 hours or longer, about 6 hours or longer, about 8 hours or longer, about 10 hours or longer, about 12 hours or longer, about 14 hours or longer, about 16 hours or longer, about 18 hours or longer, about 20 hours or longer, about 22 hours or longer, or about 24 hours or longer. In some embodiments, the reaction time is about 2 hours to about 48 hours, such as about 4 hours to about 36 hours.

In certain embodiments, the amount of time for which the reaction conducted may be that amount of time required to convert a given percentage of one of the reactants (e.g., the first nucleophile) in the reaction mixture to adduct form. For example, in one embodiment, the reaction mixture is reacted to about 20% or less free (i.e., unreacted) first nucleophile by weight, based on total first nucleophile added to the reaction mixture or to about 10% or less or 5% or less free first nucleophile by weight, based on total first nucleophile added to the reaction mixture. For example, where the reactants comprise NBPT as the first nucleophile, the reaction mixture can be reacted to about 20% or less, about 10% or less, or about 5% or less free NBPT by weight, based on NBPT added to the reaction mixture. Accordingly, in some embodiments, the method of producing an adduct as described herein further comprises monitoring the amount of free NBPT remaining over the course of the reaction and evaluating the completeness of reaction based on the amount of free reactant (i.e., free first nucleophile, free second nucleophile, or free electrophile) in comparison to the desired maximum free content of that reactant by weight to be included in the reaction product.

It is noted that the particular reactants (i.e., first and second nucleophiles, electrophile, and optional solvent) may affect the reaction conditions required to produce the reaction product. For example, reaction of components in one solvent may be more efficient than reaction of those components in a different solvent and it is understood that, accordingly, less time and/or lower temperature may be required for adduct formation in the former case. Also, where a catalyst is employed, less time and/or lower temperature may be required for adduct formation. It is also noted that, in some embodiments, employing different reaction conditions can have an effect on the amount and/or type(s) of various adducts formed during the reaction.

The reaction product can comprise various other components in addition to the adduct(s). It is to be understood that other components that may be present in the reaction product can be a result of the specific method used to produce the reaction product and, particularly, of the amount of each reactant included in the reaction mixture. For example, where the reaction conditions are such that there is an excess of one or two reactants, the reaction product may comprise free reactant (i.e., reactant which is not incorporated into an adduct). In various embodiments, the reaction product can comprise at least some percent by weight of one or more components selected from the group consisting of free NBPT, free formaldehyde, free urea, free urea-formaldehyde products (e.g., UFP), catalyst (e.g., MAP, DAP, or MAS), impurities (e.g., arising from the grade of reactants used), solvent, water, and combinations thereof. The relative amounts of such components can vary, with exemplary amounts and ratios disclosed below.

The reaction products disclosed herein can include widely varying mole percentages of the reactants disclosed herein, i.e., first nucleophile, second nucleophile, and electrophile (including complexed and free forms of each component, e.g., as determined by elemental analysis). Similarly, the reaction products disclosed herein can have widely varying molar ratios, particularly as the method of producing the adduct-containing compositions can vary. In some specific embodiments, the reaction products can have a molar ratio of about 1:0.5 to about 1:2 first nucleophile:second nucleophile (including complexed and free forms of each component, e.g., as determined by elemental analysis). In certain embodiments, urea is used in great excess as the second nucleophile with respect to the other reactants; consequently, in such embodiments, the molar ratio of first nucleophile:second nucleophile is significantly lower.

In some specific embodiments, the reaction products can have a molar ratio of about 1:0.5 to about 1:2 first nucleophile:electrophile (including complexed and free forms of each component, e.g., as determined by elemental analysis). Again, in some embodiments, the electrophile (e.g., aldehyde) is present in significant excess with respect to the first nucleophile and, in such embodiments, the molar ratio of first nucleophile:electrophile is significantly lower.

Reaction products disclosed herein that contain one or more urease inhibitors can advantageously exhibit effective urease inhibition and, in preferred embodiments, can exhibit slow release of urease inhibitor, providing extended urease inhibition properties. Accordingly, the urease inhibition exhibited by these reaction products can be achieved over a longer period of time than that exhibited by a comparable composition comprising only free (i.e., unreacted) urease inhibitor. Surprisingly, the reaction products, in some embodiments, can exhibit effective urease inhibition even at urease inhibitor levels that have been established as ineffective. In other words, a reaction product prepared using a given amount of urease inhibitor can, in some embodiments, exhibit effective urease inhibition even where a comparable composition comprising that same amount of urease inhibitor in free (i.e., unreacted) form does not show significant urease inhibition.

Reaction products disclosed herein that contain one or more nitrification inhibitors can advantageously exhibit effective nitrification inhibition and, in preferred embodiments, can exhibit slow release of nitrification inhibitor, providing extended nitrification inhibition properties. Accordingly, the nitrification inhibition exhibited by these reaction products can be achieved over a longer period of time than that exhibited by a comparable composition comprising only free (i.e., unreacted) nitrification inhibitor.

The reaction product obtained according to the methods disclosed herein can be used or stored for later use in the form in which it is provided, can be treated in some manner before being used or stored for later use (e.g., to provide it in a different form or to isolate one or more components therefrom), and/or can be combined with other components before being used or stored for later use. Various compositions comprising at least a portion of the reaction products disclosed herein are disclosed herein below.

For example, in one embodiment, the reaction product is maintained substantially in the form in which it is provided following reaction (e.g., in undiluted liquid or solid form, in solution form, in suspension/dispersion form, in the form of urea-based granules comprising the adduct, and the like). As noted above, such forms can, in some embodiments, comprise other components, e.g., residual reactants and/or solvent. The specific form of these as-formed reaction products may, in certain embodiments, be further modified prior to use and/or storage, e.g., by concentrating solution or suspension/dispersion forms by removing solvent therefrom, by diluting any of the forms by adding one or more solvents thereto, by solubilizing solid forms, or by contacting a solid, undiluted liquid, solution, or suspension/dispersion form with a solid support so as to provide the reaction product in solid form. In one particular embodiment, the reaction product is provided in homogenous solution form.

In another embodiment, the reaction product is treated so as to isolate one or more adducts therefrom. For example, the reaction product can be treated so as to remove any or all components other than the adducts from the reaction product to obtain a mixture comprising all adducts, a mixture comprising some adducts, or one or more single, isolated adducts. Such isolated mixtures or single adducts can be provided in their natural forms (e.g., in solid or liquid, substantially pure form) or can be treated as described with regard to the as-formed reaction products modified prior to use or storage (e.g., to provide a solution or suspension/dispersion of the adduct or adducts by adding one or more solvents thereto, or to provide an adduct or adduct mixture in solid form by contacting the adduct or adduct mixture in solid, undiluted liquid, solution, or suspension/dispersion form with a solid support).

In a further embodiment, the reaction product (as-formed, or modified as noted above) or the isolated adduct(s) (as-provided, or modified as noted above) can be combined with one or more other components. For example, certain compositions are provided which comprise the reaction product admixed with one or more other components, e.g., one or more nitrogen sources (e.g., urea or a urea formaldehyde product) or free NBPT. Certain compositions are provided which comprise the one or more isolated adducts admixed with one or more other components, e.g., one or more nitrogen sources (e.g., urea or a urea formaldehyde product) or free NBPT. Again, any of these combinations can be in varying forms (e.g., in solid form, undiluted liquid form, solution form, dispersion/suspension form, and the like).

In some embodiments, a reaction product as disclosed herein can be combined with a fertilizer material. As used herein, a "fertilizer material" can include any conventional plant fertilizer acceptable for use for plant nutrition. In some embodiments, the fertilizer material can include fertilizer ingredients such as nitrogen, phosphorus, potassium, sulfur, silicon, magnesium, calcium, manganese, boron, iron, like materials, and combinations thereof. Non-limiting examples of fertilizer materials that can be used according to the present disclosure include: urea; ammonium nitrate; ammonium magnesium nitrate; ammonium chloride; ammonium sulfate; ammonium phosphate; sodium nitrate; calcium nitrate; potassium nitrate; lime nitrogen; urea-form; crotonylidene diurea (CDU); isobutylidene diurea (IBDU); guanylurea (GU); phosphate fertilizer (e.g., calcium superphosphate, concentrated superphosphate, fused phosphate, humic acid phosphorus fertilizer, calcined phosphate, calcined concentrated phosphate, magnesium superphosphate, ammonium polyphosphate, potassium metaphosphate, calcium metaphosphate, magnesium phosphate, ammonium sulfate phosphate, ammonium potassium nitrate phosphate, and ammonium chloride phosphate); potash fertilizer (e.g., potassium chloride, potassium sulfate, potassium sodium sulfate, potassium sulfate magnesia, potassium bicarbonate, and potassium phosphate); muriate of potash (MOP), which refers to potassium containing compositions which can include potassium chloride, potassium carbonate, potassium hydroxide, potassium chlorate, potassium nitrate, potassium sulfate, potassium permanganate, and the like; sulfate of potash (SOP), a composition of ca. 50% potassium oxide ($K_2O$); silicate fertilizer (e.g., calcium silicate); magnesium fertilizer (e.g., magnesium sulfate and magnesium chloride); calcium fertilizer (e.g., calcium oxide, calcium hydroxide, and calcium carbonate); manganese fertilizer (e.g., manganese sulfate, manganese sulfate magnesia, and manganese slag); boron fertilizer (e.g., boric acid and borates); iron fertilizer (e.g., slag); and K-Mag, which is a potassium, magnesium, and sulfur based fertilizer.

As-Formed Reaction Product

As described in detail above, the reaction products provided herein can comprise varying amounts of adduct(s) and can further comprise varying amounts of other components.

The particular makeup of the reaction product can determine the methods of use for which that reaction product is particularly suited.

For example, where a reaction product is provided that comprises a significant free urea content, the reaction product (in varying physical forms, e.g., as described above) can be employed as a fertilizer composition. For example, although not intending to be limited, reaction products comprising at least about 50%, at least about 60%, at least about 70%, at least about 80%, at least about 90%, at least about 95%, at least about 98%, or at least about 99% by weight urea can be used as fertilizer compositions. As the reaction products can contain varying amounts of urea and/or urea-formaldehyde product, the amount of the reaction product to be applied as a fertilizer composition can vary accordingly. The rate at which such compositions are applied to soil may, in some embodiments, be identical to the rate at which urea is currently used for a given application or can be scaled accordingly (e.g., based on the weight percent of urea contained within the reaction product).

A reaction product comprising a high concentration of urea can broadly be used in all agricultural applications in which urea is currently used. These applications include a very wide range of crop and turf species, tillage systems, and fertilizer placement methods. The compositions disclosed herein are useful for fertilizing a wide variety of seeds and plants, including seeds used to grow crops for human consumption, for silage, or for other agricultural uses. Indeed, virtually any seed or plant can be treated in accordance with the present invention using the compositions of the present invention, such as cereals, vegetables, ornamentals, conifers, coffee, turf grasses, forages and fruits, including citrus. Plants that can be treated include grains such as barley, oats and corn, sunflower, sugar beets, rape, safflower, flax, canary grass, tomatoes, cotton seed, peanuts, soybean, wheat, rice, alfalfa, sorghum, bean, sugar cane, broccoli, cabbage and carrot. Application of a reaction product containing a significant urea concentration to soil and/or plants can increase the nitrogen uptake by plants, enhance crop yields, and minimize the loss of nitrogen from the soil. Such reaction products can be useful in fertilizing and inhibiting urease and/or inhibiting nitrification in various types of soils.

In some embodiments, the reaction product is used (in varying forms, e.g., as described above, including in isolated adduct form) in combination with one or more fertilizer compositions. Such methods are applicable both for reaction products comprising a significant urea concentration and reaction products comprising a lower urea concentration (including reaction products comprising little to no free urea). For example, the reaction product can be applied to the soil before, concurrently with, or after application of a nitrogen-based fertilizer composition. The reaction product can be combined with the fertilizer composition, e.g., within the soil, on or about the surface of the soil, or a combination thereof. The urea can include any of the types of urea disclosed hereinabove, such as free urea, urea-formaldehyde products, and the like and additionally can include various substituted ureas. Another suitable urea source can be or can include animal waste(s) such as urine and/or manure produced by one or more animals, e.g., cows, sheep, chickens, buffalo, turkeys, goats, pigs, horses, and the like.

In some embodiments, the urea source can be or can include animal waste such as urine and/or manure deposited on and/or in the soil or the nitrogen source can be or can include a fertilizer product previously applied to the soil. As such, the reaction product can be applied to the soil and mixed with the animal waste and/or previously applied fertilizer(s) on the surface of and/or within the soil. The reaction product can be applied to the soil before, during, and/or after the animal waste and/or fertilizer(s) are deposited on/in the soil. In another example, the urea source can be or can include animal waste such as urine and/or manure that can be collected and placed within a holding tank, pond, or the like, and the reaction product can be added to the animal waste to provide a mixture. The resulting mixture can then be deposited about the soil to act as a fertilizer therein.

In some embodiments, the reaction product can be in the form of a UFC composition. The urea-formaldehyde concentrate can be defined by comprising urea and formaldehyde in a total amount of at least 50% by weight or greater, at least 60% by weight or greater, at least 75% by weight or greater, or at least 80% by weight or greater, such as about 50% to about 60% by weight, about 50% to about 75% by weight, about 50% to about 80% by weight, about 50% to 100% by weight, about 60% to about 75% by weight, about 60% to about 80% by weight, about 60% to 100% by weight, about 75% to about 80% by weight, about 75% to 100% by weight, or about 80% to 100% by weight. More particularly, a UFC can comprise formaldehyde in an amount of at least 45% by weight or greater, at least 50% by weight or greater, or at least 55% by weight or greater, such as about 45% to about 80% by weight, about 50% to about 70% by weight, or about 50% to about 65% by weight. Further, a UFC can comprise urea in an amount of at least 10% by weight or greater, at least 15% by weight or greater, or at least 20% by weight or greater, such as about 10% to about 50% by weight, about 15% to about 45% by weight, or about 20% to about 40% by weight. The UFC can comprise a solvent, such as water, in an amount that is less than 50% by weight, less than about 40% by weight, or less than about 30% by weight, such as about 1% to about 40% by weight, about 2% to about 30% by weight, or about 5% to about 25% by weight. As non-limiting examples, UFC 80 and UFC 85 are commonly known formulations in the art wherein the UFC 80 is formed of about 57% by weight formaldehyde, about 23% by weight urea, and about 20% by weight water, and the UFC 85 is formed of about 60% by weight formaldehyde, about 25% by weight urea, and about 15% by weight water. In some embodiments, a UFC can comprise about 50% by weight to about 70% by weight formaldehyde, about 15% by weight to about 30% by weight urea, and about 5% by weight to about 30% by weight water.

Reaction Product+Free NBPT

In certain embodiments, the reaction product (in varying forms, e.g., as described above, including in isolated adduct form) can be combined with free urease inhibitor (e.g., including, but not limited to, additional free NBPT). The reaction product and free urease inhibitor can, in some embodiments, be combined during use (e.g., the reaction product can be applied to the soil before, concurrently with, or after application of free NBPT).

In certain embodiments, the reaction product and free urease inhibitor can be provided within a single composition. The free urease inhibitor combined with the reaction product can be the same urease inhibitor or a different urease inhibitor than that present in the adduct or can be a combination of the same urease inhibitor and a different urease inhibitor. In such compositions, the free urease inhibitor (e.g., NBPT) can be present in varying amounts. The adduct and free urease inhibitor can be provided in roughly equivalent amounts, the amount of NBPT may be greater than the amount of adduct, or the amount of NBPT may be less than the amount of adduct. In some embodiments, the molar ratio of NBPT:adduct is about 1:1 to about 1:10, e.g., about 1:1 to about 1:9, about 1:1 to about 1:8, about 1:1 to about 1:7, about 1:1 to about 1:6, about 1:1 to about 1:5, about 1:1 to about 1:4, about 1:1 to about 1:3, or about 1:1 to about 1:2. In other embodiments, the molar ratio may be about 10:1 to about 1:1, e.g., about 9:1 to about 1:1, about 8:1 to about 1:1, about 7:1 to about 1:1, about 6:1 to about 1:1, about 5:1 to about 1:1, about 4:1 to about 1:1, about 3:1 to about 1:1, or about 2:1 to about 1:1. Further, the molar ration may be about 1:5 to about 5:1, about 1:4 to about 4:1, about 1:3 to about 3:1, or about 1:2 to about 2:1.

As noted above, the reaction product disclosed herein may, in some embodiments, already contain some percentage of free (unreacted) NBPT, wherein NBPT was employed as the first nucleophile (but did not react completely under the reaction conditions to form an adduct). Accordingly, in some embodiments, free NBPT can be added to the reaction product to bring the total amount of free NBPT to within the desired range. In other embodiments, little to no free NBPT is understood to be present in the reaction product (e.g., where NBPT was not employed as a reactant and/or wherein single adducts have been isolated from excess reactant); accordingly, sufficient free NBPT may, in some embodiments, be added to bring the free NBPT content of the resulting composition within the ranges referenced above. Surprisingly, NBPT-containing adducts as disclosed herein in combination with free NBPT can, in some embodiments, exhibit synergistic activity. For example, when a reaction product is combined with free NBPT, the resulting composition can exhibit greater urease inhibition than would be expected based on the urease inhibition of a comparable amount of NBPT, all in free (unreacted) form.

In certain embodiments, reaction product/free NBPT compositions can be directly employed as fertilizer compositions (i.e., where the reaction product comprises a significant free urea content and/or a significant urea-formaldehyde product content). However, more commonly, such reaction product/free NBPT compositions are used in combination with a nitrogen source. In such embodiments, a composition comprising the reaction product and free NBPT can be applied in varying forms (e.g., in liquid, solution, dispersion/suspension, or solid form) to the soil before, concurrently with, or after application of a nitrogen-based fertilizer composition. The nitrogen-based fertilizer can include, for example, any of the types of urea and urea-formaldehyde products disclosed hereinabove. The composition can be combined with the fertilizer composition, e.g., within the soil, on or about the surface of the soil, or a combination thereof. The reaction product/free NBPT composition advantageously provides effective urease inhibition with regard to the nitrogen-based fertilizer composition.

Reaction Product+Urea

Reaction products as disclosed herein can, in some embodiments, be combined with a nitrogen source to provide an adduct-containing fertilizer composition. For example, the reaction product (in various forms, including isolated adduct form) can, in some embodiments, be combined (e.g., mixed, blended, or otherwise combined) with one or more nitrogen sources (e.g., urea or urea-formaldehyde products). The relative amounts of adduct and urea in such a fertilizer composition can vary, and in certain embodiments, the amount of adduct can be, for example, within the range of about 1 ppm to about 10,000 ppm adduct in the fertilizer composition. A composition provided by combining the reaction product with urea can provide a fertilizer composition comprising up to about 95% by weight urea, up to about 98% by weight urea, up to about 99% by weight urea, up to about 99.5% by weight urea or up to about 99.9% by weight urea, e.g., about 95% to about 99.9% by weight urea, about 98% to about 99.9% by weight urea, or about 99% to about 99.9% by weight urea, and the like.

In certain embodiments, the reaction product can be blended directly with granulated urea or can be used as an additive to liquid (molten) urea. The combining of reaction product with urea can be done at ambient temperature or at elevated temperature, e.g., at least about 50° C., at least about 60° C., at least about 70° C., at least about 80° C., at least about 90° C., or at least about 100° C., such as about 20° C. to about 150° C., about 50° C. to about 150° C., about 70° C. to about 145° C., about 80° C. to about 140° C., about 90° C. to about 135° C., or about 100° C. to about 130° C. Advantageously, in some embodiments, the reaction product can be combined with urea under conditions of conventional urea manufacturing generally including temperatures at which urea is in molten form, e.g., temperatures of about 130° C. to about 135° C., or greater. In such embodiments, it is beneficial to ensure that sufficient mixing is employed during this combining step so that the adduct is substantially homogeneously distributed within the molten urea, particularly before the urea melt cools and solidifies in the subsequent granulation step.

The reaction product can be combined with the urea in various forms, e.g., in liquid form, as a solution or suspension/dispersion, or in solid form. The amount of reaction product added to urea in accordance with this embodiment depends on the desired adduct content of the resulting fertilizer composition and on the adduct content of the reaction product, and can be readily calculated by those skilled in the art. Other components may be present in the adduct-containing fertilizer composition, which can be intentionally added or which can be inherently present in one or more of the composition components. For example, the compositions can comprise, in addition to the urea and reaction product components, some moisture, urea synthesis byproducts, solvent(s), and as noted further herein, may optionally contain other additives, such as dye(s), NBPT, stabilizer(s), and/or micronutrient(s).

Other Optional Components (Applicable to all Compositions Disclosed Herein)

Other optional components may be used in compositions of the present invention. Examples of other such components include but are not limited to: nitrification inhibitors; conditioners; xanthan gum; calcium carbonate (agricultural lime) in its various forms for adding weight and/or raising the pH of acidic soils; metal containing compounds and minerals such as gypsum, metal silicates, and chelates of various micronutrient metals such as iron, zinc and manganese; talc; elemental sulfur; activated carbon, which may act as a "safener" to protect against potentially harmful chemicals in the soil; plant protectants; nutrients; nutrient stabilizers; super absorbent polymers; wicking agents; wetting agents; plant stimulants to accelerate growth; inorganic nitrogen, phosphorus, potassium (N—P—K) type fertilizers; sources of phosphorus; sources of potassium; organic fertilizers; surfactants, such as alkylaryl polyether alcohols; initiators; stabilizers; cross linkers; antioxidants; UV stabilizers; reducing agents; dyes, such as blue dye (FD & C blue #1); pesticides; herbicides; fungicides; and plasticizers. The content of the additional component(s) disclosed herein can be from about 1 to about 75 percent by weight of the composition and depends, in part, on the desired function of the additional component(s) and the makeup of the composition to which the additional component(s) are added.

Examples of conditioners include but are not limited to tricalcium phosphate, sodium bicarbonate, sodium ferricyanide, potassium ferricyanide, bone phosphate, sodium silicate, silicon dioxide, calcium silicate, talcum powder, bentonite, calcium aluminum silicate, stearic acid, and polyacrylate powder. Examples of plant protectants and nutrient stabilizers include silicon dioxide and the like. Examples of nutrients include, but are not limited to, phosphorus and potassium based nutrients. A commercially available fertilizer nutrient can include, for example, K-Fol 0-40-53, which is a solution that contains 40 wt % phosphate and 53 wt % potassium, which is manufactured and distributed by GBS Biosciences, LLC.

Nitrification inhibitors are compounds which inhibit the conversion of ammonium to nitrate and reduce nitrogen losses in the soil. Examples of nitrification inhibitors include, but are not limited to, dicyandiamide (DCD), and the like. Although the compositions disclosed herein can include DCD (in free form or within one or more adducts, as disclosed herein above), in certain embodiments, the compositions are substantially free of DCD. "Substantially free" of DCD or "substantially no" DCD means that either no DCD can be detected in the mixture or, if DCD can be detected, it is (1) present in <1% w/w (preferably, <0.85% w/w, <0.80% w/w, <0.75% w/w, <0.5% w/w, or <0.25% w/w); and (2) does not produce effects characteristic of DCD at higher proportions. For example, a composition having substantially no DCD would not produce the environmental effects of exposure to concentrated or pure DCD even if a trace amount of DCD could be detected in the mixture. Certain exemplary compositions can have a DCD content of less than about 0.85% by weight, less than about 0.80% by weight, less than about 0.75% by weight, less than about 0.5% by weight, or less than about 0.25% by weight.

EXAMPLES

In order to provide a better understanding of the foregoing discussion, the following non-limiting examples are offered.

Although the examples may be directed to specific embodiments, they are not to be viewed as limiting the invention in any specific respect. All parts, proportions, and percentages are by weight unless otherwise indicated.

Generally, LC-MS analysis was performed on an Agilent 6330 Ion trap equipped with an electrospray ionization (ESI) probe. The heated capillary temperature was held at 350° C., the nebulizer was set to 55 PSI and the dry gas set to 12 L/min. The spray voltage was set to 3.5 kV. A sample weighing 50-65 mg was weighed into a scintillation vial and dissolved with minimal 1:1 acetonitrile/water (~0.75 mL). The solution was transferred to a 100 mL volumetric flask. The scintillation vial was rinsed seven times with diluent (3:7 acetonitrile/water) and all rinses were transferred to the volumetric flask while sonicating the volumetric flask. The volumetric flask was diluted to the mark with diluent, mixed, and 1 mL of the solution was transferred to an autosampler vial.

Example 1: Synthetic Preparation of Adducts (Method A)

As a representative example, to a solution of N-(n-butyl) thiophosphoric triamide (NBPT, 1 equiv.) in N-methyl-2-pyrrolidone (NMP, ~72 wt. %) was added a second nucleophile (1 equiv.), followed by an electrophile, here, formalin (50% aq. solution of formaldehyde, 1 equiv.), which initiates the reaction. After being stirred for 3 h at 40° C. and then cooled down to room temperature, a homogeneous solution was obtained, containing the desired adducts (Table 1). Specific synthetic preparations for the various Samples shown in Table 1 and 3 are also provided herein below.

TABLE 1

Adducts obtained by the reaction of Nucleophiles 1 and 2 in the presence of Electrophile (aldehyde)

| Sample | Nuc. 1 | Electrophile | Nuc. 2 | NBPT Conversion[a] (%) | Adduct(s) | LC-MS Characterization (ESI, m/z) |
|---|---|---|---|---|---|---|
| 1 | NBPT | HCHO | DCD | 91 | MW = 263 | $t_R$ = 14.1 min, 264 [M + H]$^+$, $t_R$ = 15.1 min, 264 [M + H]$^+$ |
| 2 | NBPT | HCHO | 3,5-DMP | n/a[b] | MW = 275; MW = 383 | $t_R$ = 22.7 min, 276 [M + H]$^+$, $t_R$ = 28.3 min, 406 [M + Na]$^+$ |

TABLE 1-continued

Adducts obtained by the reaction of Nucleophiles 1 and 2 in the presence of Electrophile (aldehyde)

| Sample | Nuc. 1 | Electrophile | Nuc. 2 | NBPT Conversion[a] (%) | Adduct(s) | LC-MS Characterization (ESI, m/z) |
|---|---|---|---|---|---|---|
| 3 | NBPT | HCHO | 4-Amino 1,2,4-triazole | 72 | MW = 263 | $t_R$ = 12.6 min, 264 [M + H]$^+$, |
| 4 | NBPT | HCHO | Thiourea | 88 | MW = 255; MW = 343 | $t_R$ = 15.7 min, 278 [M + Na]$^+$, $t_R$ = 16.3 min, 366 [M + Na]$^+$, $t_R$ = 17.5 min, 366 [M + Na]$^+$ |
| 5 | NBPT | MeCHO | 4-Amino 1,2,4-triazole | 15 | MW = 277 | $t_R$ = 13.8 min, 278 [M + H]$^+$, $t_R$ = 15.2 min, 278 [M + H]$^+$ |
| 6 | 3,5-DMP | HCHO | Urea | n/a | MW = 168 | $t_R$ = 6.2 min, 169 [M + H]$^+$ |
| 7 | NBPT | MeCHO | DCD | 37 | MW = 277 | $t_R$ = 16.5 min, 278 [M + H]$^+$ |

NBPT: N-(n-butyl)thiophosphoric triamide;
DCD: dicyanoguanidine; 3,5-DMP: 3,5-dimethylpyrazole;
HCHO: formaldehyde;
MeCHO: acetaldehyde
[a]The NBPT content remaining in the reaction mixture was quantified by HPLC
[b]NBPT and 3,5-DMP co-elute using the HPLC method; therefore, NBPT conversion was not determined

Example 1.1 (Sample 1)

According to the general synthesis (Example 1), N-(n-butyl)thiophosphoric triamide (NBPT, 15 g, 89.7 mmol) and dicyandiamide (DCD, 7.5 g, 89.7 mmol, 1 equiv.) were stirred in N-methyl-2-pyrrolidone (NMP, 70.1 mL) at 40° C. in the presence of formalin (50% aq. HCHO, 4.8 mL, 89.7 mmol, 1 equiv.). LC-MS (ESI, m/z) $t_R$=14.1 min, 264 $[M+H]^+$, $t_R$=15.1 min, 264 $[M+H]^+$.

Example 1.2 (Sample 2)

According to the general synthesis (Example 1), 15 g (89.7 mmol) of NBPT (15 g, 89.7 mmol) and of 3,5-dimethylpyrazole (8.6 g, 89.7 mmol, 1 equiv) were stirred in NMP (69.1 mL) at 40° C. in the presence of formalin (50% aq. HCHO, 4.8 mL, 89.7 mmol, 1 equiv). LC-MS (ESI, m/z) $t_R$=22.7 min, 276 $[M+H]^+$, $t_R$=28.3 min, 406 $[M+H]^+$.

Example 1.3 (Sample 3)

According to the general synthesis (Example 1), NBPT (15.0 g, 89.7 mmol) and 4-amino-1,2,4-triazole (7.5 g, 89.7 mmol, 1 equiv) were stirred in NMP (70.1 mL) at 40° C. in the presence of formalin 4.8 mL HCHO (50% aq. HCHO, 4.8 mL, 89.7 mmol, 1 equiv). LC-MS (ESI, m/z $t_R$=12.6 min, 264 $[M+H]^+$, $t_R$=25.2 min, 359 $[M]^+$, $t_R$=26.0 min, 359 $[M]^+$, $t_R$=27.8 min, 359 $[M]^+$.

Example 1.4 (Sample 4)

According to the general synthesis (Example 1), NBPT (15.0 g, 89.7 mmol) and thiourea (6.8 g, 89.7 mmol, 1 equiv) were stirred in NMP (70.8 mL) at 40° C. in the presence of formalin (50% aq. HCHO, 4.8 mL, 89.7 mmol, 1 equiv). LC-MS (ESI, m/z) $t_R$=15.7 min, 278 $[M+Na]^+$, $t_R$=16.3 min, 366 $[M+Na]^+$, $t_R$=17.5 min, 366 $[M+Na]^+$.

Example 1.5 (Sample 5)

According to the general synthesis (Example 1), NBPT (2.31 g, 13.8 mmol) and 4-amino-1,2,4-triazole (1.16 g, 13.8 mmol, 1 equiv) were stirred in NMP (10.7 mL) at 40° C. in the presence of acetaldehyde (40% aq. solution, 1.8 mL, 13.8 mmol, 1 equiv). LC-MS (ESI, m/z) $t_R$=13.8 min, 278 $[M+H]^+$, $t_R$=15.2 min, 278 $[M+H]^+$.

Example 1.6 (Sample 6)

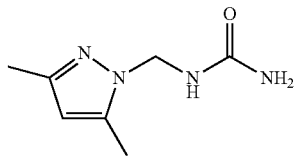

According to the general synthesis (Example 1), 3,5-dimethylpyrazole (2.31 g, 24.0 mmol) and urea (1.44 g, 24.0 mmol, 1 equiv) were stirred in NMP (10 mL) at 40° C. in the presence of formalin (50% aq. solution, 1.3 mL, 24.0 mmol, 1 equiv). LC-MS (ESI, m/z) $t_R$=6.2 min, 169 $[M+H]^+$.

Example 1.7 (Sample 7)

According to the general synthesis (Example 1), NBPT (2.31 g, 13.8 mmol) and dicyandiamide (1.16 g, 13.8 mmol, 1 equiv) were stirred in NMP (10.1 mL) at 50° C. in the presence of acetaldehyde (40% aq. solution, 1.8 mL, 13.8 mmol, 1 equiv). LC-MS (ESI, m/z) $t_R$=16.5 min, 278 $[M+H]^+$.

Example 2: Synthetic Preparation of Adducts (Method B)

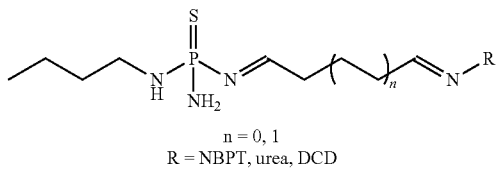

n = 0, 1
R = NBPT, urea, DCD

As a representative example, to a solution of N-(n-butyl) thiophosphoric triamide (NBPT, 1 equiv.) in N-methyl-2-pyrrolidone (NMP, ~62 wt. %) was added a second nucleophile (1 equiv.) at 40° C. The reaction was initiated by addition of a dialdehyde (1 equiv.). After being stirred for 3 h at 40° C. and then cooled down to room temperature, a homogeneous solution was obtained, containing the desired products. Specific synthetic preparations for the various Samples shown in Table 2 are also provided herein below.

TABLE 2

Adducts obtained by the reaction of Nucleophiles 1 and 2 in the presence of Electrophile (dialdehyde)

| Sample | Nuc. #1 1 equiv | Electrophile 1 equiv | Nuc. #2 1 equiv | NBPT Conversion[a] (%) | Adduct(s) | LC-MS Characterization (ESI, m/z) |
|---|---|---|---|---|---|---|
| 8 | NBPT | glutaraldehyde | urea | 81 | 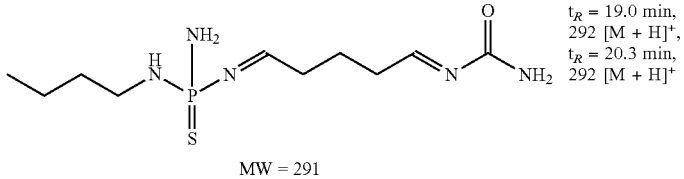 MW = 291 | $t_R$ = 19.0 min, 292 $[M + H]^+$, $t_R$ = 20.3 min, 292 $[M + H]^+$ |

TABLE 2-continued

Adducts obtained by the reaction of Nucleophiles 1 and 2 in the presence of Electrophile (dialdehyde)

| Sample | Nuc. #1 1 equiv | Electrophile 1 equiv | Nuc. #2 1 equiv | NBPT Conversion[a] (%) | Adduct(s) | LC-MS Characterization (ESI, m/z) |
|---|---|---|---|---|---|---|
| 9 | NBPT | glyoxal | — | 99 | MW = 356 | $t_R$ = 23.7 min, 357 [M + H]$^+$, $t_R$ = 24.2 min, 357 [M + H]$^+$, $t_R$ = 25.2 min, 357 [M + H]$^+$ |
| 10 | NBPT | glyoxal | DCD | 32 | MW = 273; MW = 356 | $t_R$ = 12.3 min, 274 [M + H]$^+$, $t_R$ = 14.6 min, 274 [M + H]$^+$, $t_R$ = 23.7 min, 357 [M + H]$^+$, $t_R$ = 24.2 min, 357 [M + H]$^+$, $t_R$ = 25.2 min, 357 [M + H]$^+$ |

Example 2.1 (Sample 8)

According to the general synthesis (Example 2), NBPT (15 g, 89.7 mmol) and urea (5.39 g, 89.7 mmol) were stirred in NMP (60 mL) at 40° C. in the presence of glutaraldehyde (16.2 mL, 50% aqueous solution, 89.7 mmol, 1 equiv). LC-MS (ESI, m/z) $t_R$=19.0 min, 292 [M+H]$^+$, $t_R$=20.3 min, 292 [M+H]$^+$.

Example 2.2 (Sample 9)

According to the general synthesis (Example 2), NBPT (2.3 g, 13.8 mmol) was stirred in NMP (11 mL) at 40° C. in the presence of glyoxal (40% aq. solution, 13.8 mmol, 1 equiv). LC-MS (ESI, m/z) $t_R$=23.7 min, 357 [M+H]$^+$, $t_R$=24.2 min, 357 [M+H]$^+$, $t_R$=25.2 min, 357 [M+H]$^+$.

Example 2.3 (Sample 10)

DCD (1.16 g, 13.8 mmol, 1 equiv) and glyoxal (40% aq. solution, 1.2 mL, 13.8 mmol, 1 equiv) were stirred in NMP (9.7 mL) at 40° C. After 1 hour at that temperature, NBPT (2.31 g, 13.8 mmol) was added to the reaction mixture. After being stirred for 4 h at 40° C. and then cooled down to room temperature, a homogeneous solution was obtained, containing the desired products. LC-MS (ESI, m/z) $t_R$=12.3 min, 274 [M+H]$^+$, $t_R$=14.6 min, 274 [M+H]$^+$, $t_R$=23.7 min, 357 [M+H]$^+$, $t_R$=24.2 min, 357 [M+H]$^+$, $t_R$=25.2 min, 357 [M+H]$^+$.

TABLE 3

Adducts obtained by additional reactions of Nucleophiles 1 and 2 in the presence of Electrophile

| Sample | Nuc. #1 1 equiv | Electrophile 1 equiv | Nuc. #2 1 equiv | NBPT Conversion[a] (%) | Adduct(s) | LC-MS Characterization (ESI, m/z) |
|---|---|---|---|---|---|---|
| 11 | NBPT | MeCHO | urea | 13.3 | | $t_R$ = 14.0 min, 276 [M + Na]$^+$, $t_R$ = 15.1 min, 276 [M + Na]$^+$, $t_R$ = 16.5 min, 265 [M + H]$^+$ |
| 12 | NBPT | MeCHO | thiourea | 22.7 | | $t_R$ = 16.0 min, 265 [M + H]$^+$, $t_R$ = 16.5 min, 265 [M + H]$^+$, $t_R$ = 16.8 min, 292 [M + Na]$^+$, $t_R$ = 17.0 min, 292 [M + Na]$^+$, $t_R$ = 21.7 min, |

TABLE 3-continued

Adducts obtained by additional reactions of Nucleophiles 1 and 2 in the presence of Electrophile

| Sample | Nuc. #1 1 equiv | Electrophile 1 equiv | Nuc. #2 1 equiv | NBPT Conversion$^a$ (%) | Adduct(s) | LC-MS Characterization (ESI, m/z) |
|---|---|---|---|---|---|---|
| 13 | NBPT | MeCHO | DCD | 16.0 | 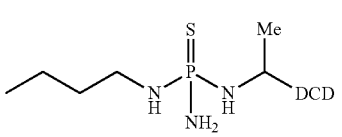 | 265 [M + H]$^+$ $t_R$ = 15.9 min, 265 [M + H]$^+$, |

Example 3.1 (Sample 11)

According to the general synthesis (Example 1), NBPT (1 equiv) and urea (1 equiv) were stirred in NMP at 40° C. in the presence of acetaldehyde (40% aq. solution, 1 equiv) for 3 hours. LC-MS (ESI, m/z) $t_R$=14.0 min, 276 [M+Na]$^+$, $t_R$=15.1 min, 276 [M+Na]$^+$, $t_R$=16.5 min, 265 [M+H]$^+$

Example 3.2 (Sample 12)

According to the general synthesis (Example 1), NBPT (1 equiv) and thiourea (1 equiv) were stirred in NMP at 40° C. in the presence of acetaldehyde (40% aq. solution, 1 equiv) for 3 hours. LC-MS (ESI, m/z) $t_R$=16.0 min, 265 [M+H]$^+$, $t_R$=16.5 min, 265 [M+H]$^+$, $t_R$=16.8 min, 292 [M+Na]$^+$, $t_R$=17.0 min, 292 [M+Na]$^+$, $t_R$=21.7 min, 265 [M+H]$^+$

Example 3.3 (Sample 13)

According to the general synthesis (Example 1), NBPT (1 equiv) and DCD (1 equiv) were stirred in NMP at 40° C. in the presence of acetaldehyde (40% aq. solution, 1 equiv) for 3 hours. LC-MS (ESI, m/z) $t_R$=15.9 min, 265 [M+H]$^+$.

Example 3: Determination of Urease Inhibition

The effectiveness of urease inhibition was measured as follows. One-half tbsp. of deionized water was used to moisten 3-4 oz. of soil of pH 4-5 in a 16 ounce glass jar. Approximately one-half tbsp. (~2 g) of NBPT- and/or adduct-treated urea granules was applied to the soil surface and the jar was sealed with a septum lid. The jar was incubated at room temperature for three days and analyzed for ammonia volatilization by inserting an ammonia-sensitive Dräger tube through the septum in the lid of the sealed container. In this way, the amount of ammonia present in the headspace of the container was quantified up to 600 ppm, the limit of the Dräger tube. In general, more effective urease inhibitors are characterized by having lower concentrations of ammonia in the headspace. All tests were run in triplicate in the presence of a positive control (i.e., untreated urea), which typically exhibits >600 ppm ammonia after 3 days following application.

Various compositions comprising NBPT and/or the adducts disclosed herein were prepared by combining NBPT and/or adducts with urea granules; and urease inhibition was determined using the methodologies described above. The tested samples are as presented below in Table 3.

TABLE 3

Samples Evaluated in Urease Inhibition Testing

| Sample | Contains Phosphorus Species # | Phosphorus Content (ppm P) | Sample | Contains Phosphorus Species # | Phosphorus Content (ppm P) |
|---|---|---|---|---|---|
| 1a | Sample 1 | 111 | 1b | Sample 1:NBPT | 55:55 |
| 2a | Sample 2 | 111 | 2b | Sample 2:NBPT | 55:55 |
| 3a | Sample 3 | 111 | 3b | Sample 3:NBPT | 55:55 |
| 4a | Sample 4 | 111 | 4b | Sample 4:NBPT | 55:55 |
| 5a | Sample 5 | 111 | 5b | Sample 5:NBPT | 55:55 |
| 6a | Sample 6 | n/a* | 6b | Sample 6:NBPT | n/a* |
| 7a | Sample 7 | 111 | 7b | Sample 7:NBPT | 55:55 |
| 8a | Sample 8 | 111 | 8b | Sample 8:NBPT | 55:55 |
| 9a | Sample 9 | 111 | 9b | Sample 9:NBPT | 55:55 |
| 10a | Sample 10 | 111 | 10b | Sample 10:NBPT | 55:55 |
| 11a | Sample 11 | 111 | 11b | Sample 11:NBPT | 55:55 |
| 12a | Sample 12 | 111 | 12b | Sample 12:NBPT | 55:55 |
| 13a | Sample 13 | 111 | 13b | Sample 13:NBPT | 55:55 |

*Sample 6 does not contain NBPT (includes 3,5-DMP and not NBPT as nucleophile and thus is not a urease inhibitor per se)

Figure 2:
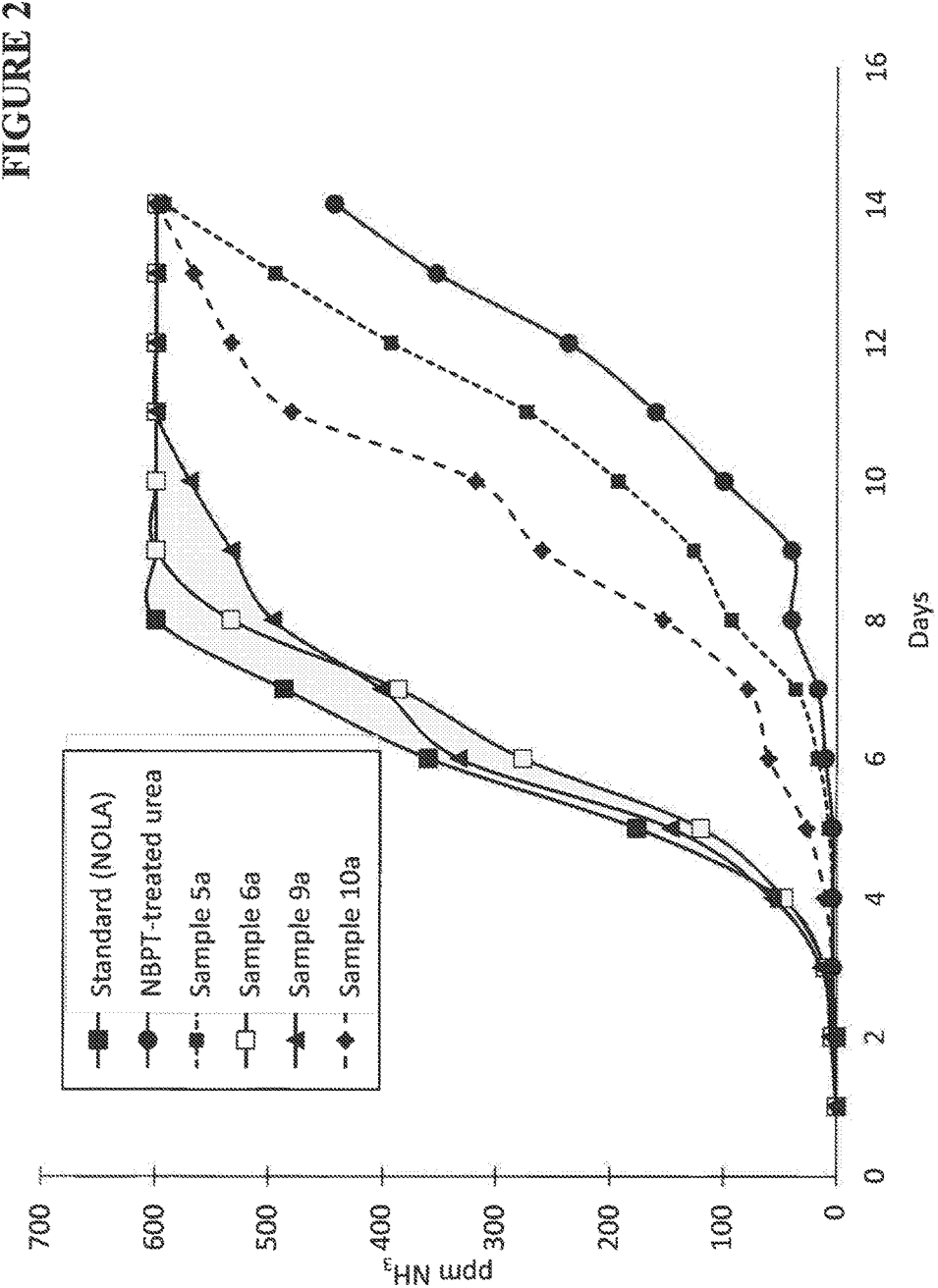
FIG. 2 is a graph of ammonia ($NH_3$) volatilization from soil samples to which other various treated ureas have been added (urea treated with NBPT adduct-containing compositions)

The data in FIGS. 1 and 2 show the effect of various urease inhibitors, namely NBPT and/or the adducts disclosed herein, on volatilization of ammonia from treated urea exposed to soil according to the method outlined above. For comparison purposes, the data is presented according to the phosphorous content (i.e. ppmP as measured by ICP), of the various inhibitors used to treat the urea. The onset of significant ammonia volatilization was arbitrarily chosen as >100 ppm.

FIGS. 1 and 2 provide data for Samples 1a, 2a, 3a, 4a, and 8a and Samples 5a, 6a, 9a, and 10a respectively (i.e., samples treated with various adduct-containing compositions as shown above in Table 3). The onset of volatilization was delayed with all treated samples compared to the positive urea control (shown as "Standard (NOLA)" in reference to the industrial fertilizer standard of New Orleans, La.). The treated samples show a >1 day improvement in ammonia volatilization over untreated urea. The data showed that the treated samples with the more unconverted NBPT displayed less volatilization.

Figure 3:
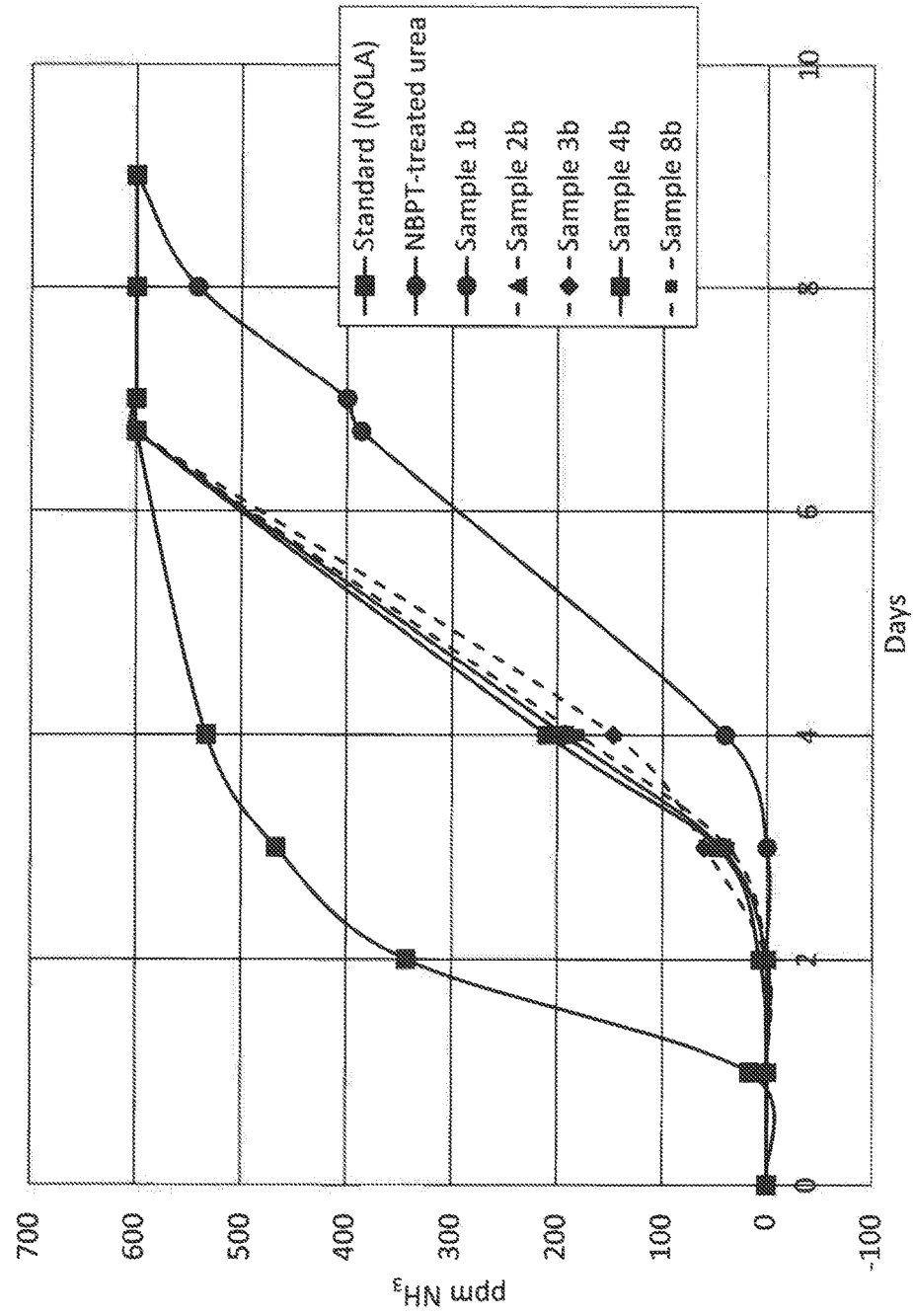
FIG. 3 is a graph of ammonia ($NH_3$) volatilization from soil samples to which various treated ureas have been added (urea treated with both free NBPT and NBPT adduct-containing compositions)
Figure 4:
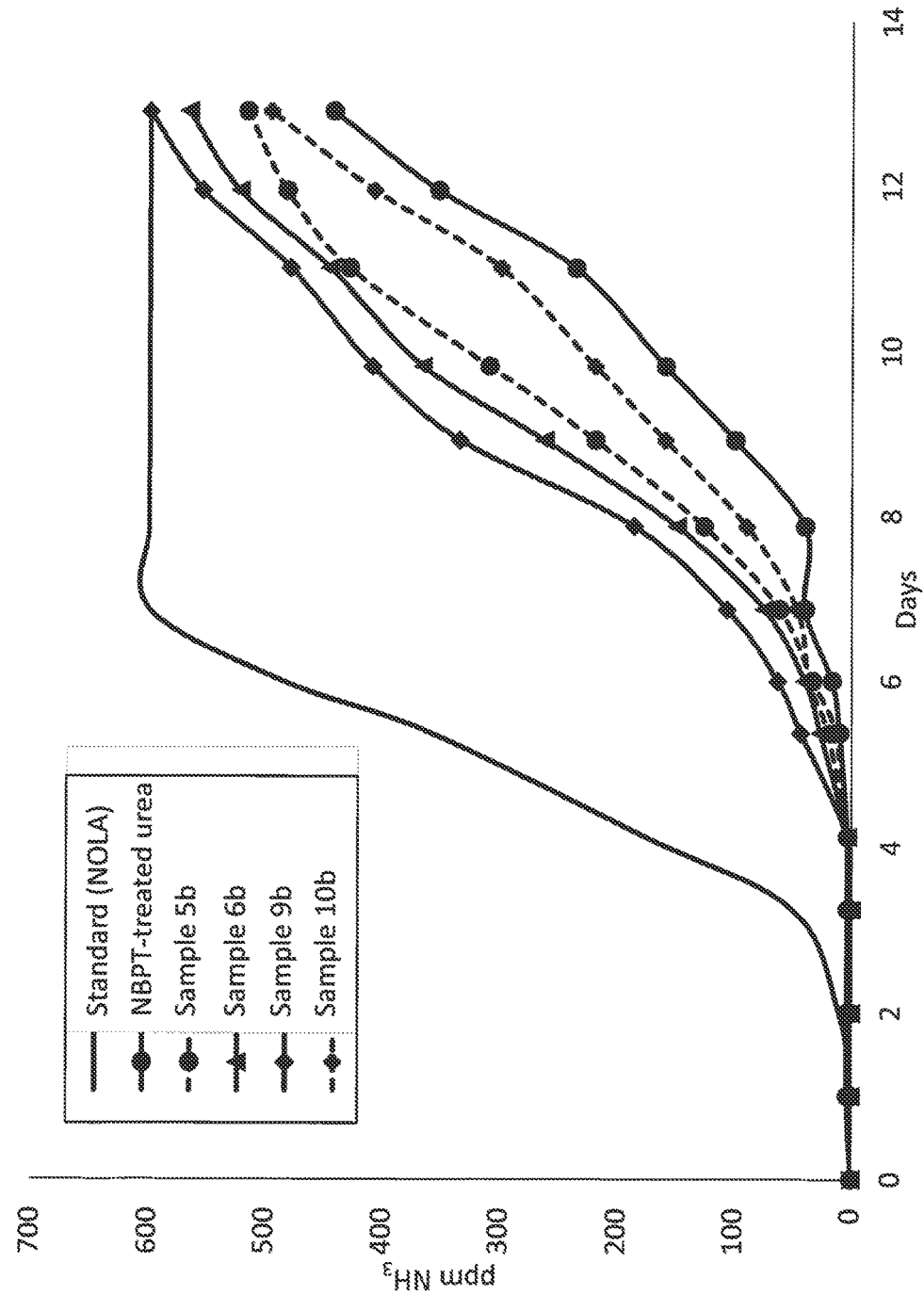
FIG. 4 is a graph of ammonia ($NH_3$) volatilization from soil samples to which other various treated ureas have been added (urea treated with both free NBPT and NBPT adduct-containing compositions)

FIGS. 3 and 4 provide data for Samples 1b, 2b, 3b, 4b, and 8b and Samples 5b, 6b 9b, and 10b respectively (i.e., samples treated with various compositions comprising a 1:1 adduct:NBPT ratio as shown above in Table 3). These compositions, as shown, are better at controlling ammonia volatilization than adducts alone. Using such compositions at a phosphorous content of 111 ppmP, a >2 days delay is observed. The 1:1 adducts:NBPT-treated urea demonstrates a synergistic benefit over adduct-only treated urea (as shown in FIGS. 1 and 2) when dosed to equivalent phosphorous levels.

Figure 5:
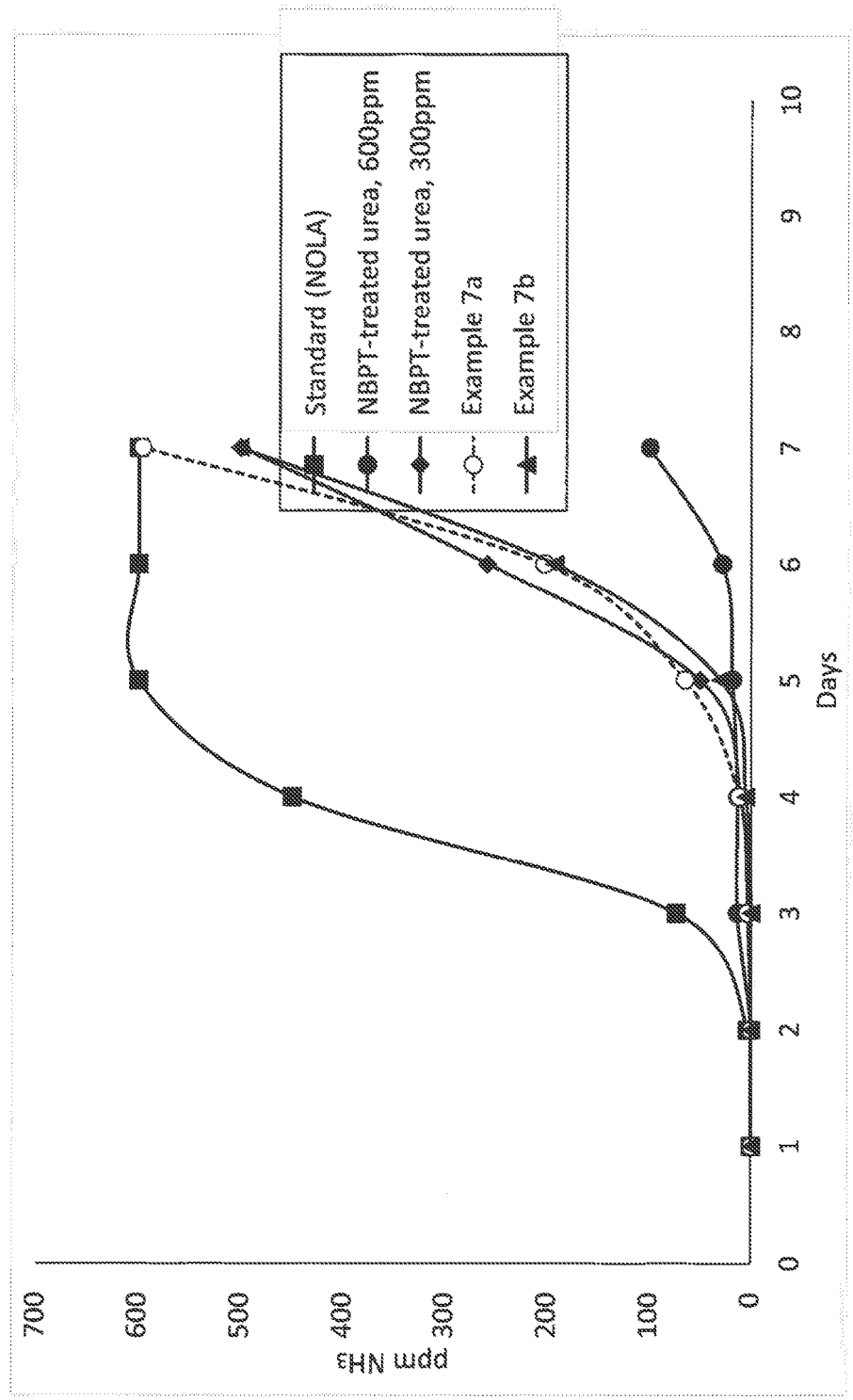
FIG. 5 is a graph of ammonia ($NH_3$) volatilization from soil samples to which further various treated ureas have been added (urea treated with NBPT-adduct containing composition and urea treated with both free NBPT and NBPT adduct-containing compositions).

FIG. 5 provides data for Samples 7a and 7b, compared against the standard urea fertilizer and NBPT-treated urea at two different concentrations. FIG. 6 provides data for Samples 11a, 11b, 12a, 12b, 13a, and 13b compared against the standard urea fertilizer and NBPT-treated urea at two different concentrations.

The invention claimed is:

1. A composition comprising:
   an adduct of Formula A or Formula B:

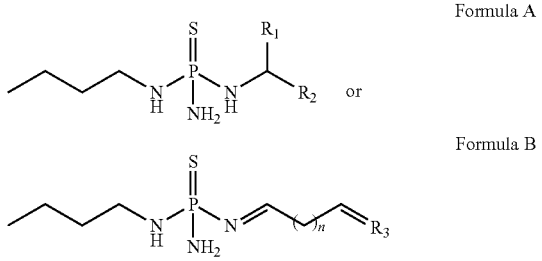

Formula A or

Formula B wherein $R^1$ is H, OH, a substituted or unsubstituted alkyl group, a substituted or unsubstituted alkenyl group, a substituted or unsubstituted alkynyl group, a substituted or unsubstituted heteroalkyl group, a substituted or unsubstituted aryl, or a substituted or unsubstituted heteroaryl;
   n is 0, 1, 2, or 3; and
   $R^2$ and $R^3$ are each independently a nucleophile, which is a nitrification inhibitor, a urease inhibitor, or urea;
   free N-(n-butyl)thiophosphoric triamide (NBPT); and
   an organic solvent selected from glycols, glycol derivatives and protected glycols,
   acetonitrile, DMSO, alkanolamines, alkylsulfones, alkyl amides, monoalcohols, dibasic esters and derivatives thereof, alkylene carbonates, monobasic esters, carboxylic acids, glycol esters, surfactants, and combinations thereof;
   wherein the molar ratio of free NBPT:adduct is about 1:1 to about 1:10.

2. The composition of claim 1, wherein the nucleophile is urea, N-(n-butyl)thiophosphoric triamide (NBPT), 2-chloro-6-trichloromethyl-pyridine, 5-ethoxy-3-trichloromethyl-1, 2, 4-thiadiazol, dicyandiamide (DCD), 4-amino-1,2,4-triazole, 3,5-2 dimethylpyrazole, 2-amino-4-chloro-6-methylpyrimidine, 1,3-benzothiazole-2-thiol, 4-amino-N-1,3-thiazol-2-ylbenzenesulfonamide, thiourea, guanidine, 3,4-dimethylpyrazole phosphate, 3,5-dimethyl pyrazole, 2, 4-diamino-6-trichloromethyl-5-triazine, polyetherionophores, 4-amino-1,2, 4-triazole, 3-mercapto-1,2,4-triazole, potassium azide, carbon bisulfide, sodium trithiocarbonate, ammonium dithiocarbamate, 2,3, dihydro-2,2-dimethyl-7-benzofuranol methyl-carbamate, N-(2,6-dimethylphenyl)-N-(methoxyacetyl)-alanine methyl ester, ammonium thiosulfate, 1-hydroxypyrazole, 2-methylpyrazole-1-carboxamide, or a combination thereof.

3. The composition of claim 1, wherein $R^1$ is H, OH, methyl, ethyl, n-propyl, iso-propyl, n-butyl, iso-butyl, pentyl, iso-pentyl, phenyl, or 2-furyl.

4. The composition of claim 1, wherein the adduct of Formula A comprises an adduct of the following formula:

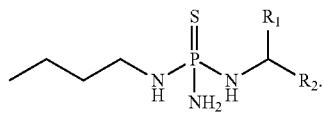

$R^1$ = H, OH, Me, Et, n-Pr, i-Pr, n-Bu,. i-Bu, pentyl, i-pentyl, Ph, 2-furyl
$R^2$ = urea, DCD, 3,5-DMP, 4-amino-1,2,4-triazole, thiourea 5. The composition of claim 1, wherein the adduct of Formula A comprises an adduct of the following formula:

(FORMULA 4A)

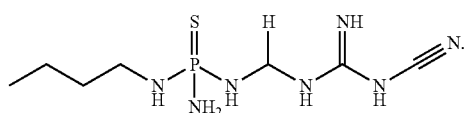

6. The composition of claim 1, wherein the adduct of Formula A comprises an adduct of the following formula:

(FORMULA 4B)

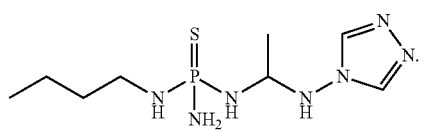

7. The composition of claim 1, wherein the molar ratio of free NBPT:adduct is about 1:1 to about 1:2.

8. The composition of claim 1, wherein the molar ratio of free NBPT:adduct is about 1:1 to about 1:4.

9. The composition of claim 1, wherein the molar ratio of free NBPT:adduct is about 1:1 to about 1:6.

10. A composition comprising:
an adduct of Formula A or Formula B

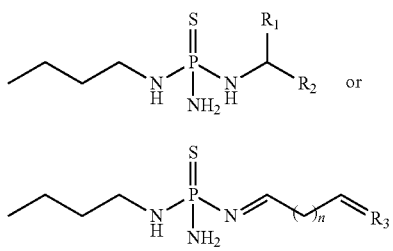

wherein R¹ is H, OH, a substituted or unsubstituted alkyl group, a substituted or unsubstituted alkenyl group, a substituted or unsubstituted alkynyl group, a substituted or unsubstituted heteroalkyl group, a substituted or unsubstituted aryl, or a substituted or unsubstituted heteroaryl;
n is 0, 1, 2, or 3; and
R² and R³ are each independently a nucleophile, which is a nitrification inhibitor, a urease inhibitor, or urea;
free N-(n-butyl)thiophosphoric triamide (NBPT); and
an organic solvent selected from the group consisting of glycols, glycol derivatives, protected glycols, glycol ethers, acetonitrile, DMSO, alkanolamines, alkylsulfones, alkyl amides, monoalcohols, dibasic esters and derivatives thereof, alkylene carbonates, monobasic esters, carboxylic acids, glycol esters, surfactants, and combinations thereof;
the composition prepared by a process comprising:
(a) providing a solution of N-(n-butyl)thiophosphoric triamide (NBPT), in the organic solvent, optionally comprising an aqueous solvent;
(b) adding a nucleophile;
(c) adding an electrophile;
(d) reacting the resulting mixture at a temperature ranging from about 25° C. to about 70° C.; and
(e) cooling the mixture to room temperature, wherein the molar ratio of free NBPT:adduct is about 1:1 to about 1:10.

11. The composition prepared by the process of claim 10, wherein the organic solvent is an N-alkyl 2-pyrrolidone, glycerol, isopropylidine glycerol, ethyl acetate, acetonitrile, DMSO, propylene glycol, benzyl alcohol, or a combination thereof.

12. The composition prepared by the process of claim 10, wherein the nucleophile is urea, N-(n-butyl)thiophosphoric triamide (NBPT), 2-chloro-6-trichloromethyl-pyridine, 5-ethoxy-3-trichloromethyl-1,2,4-thiadiazol, dicyandiamide (DCD), 4-amino-1,2,4-triazole, 3,5-dimethylpyrazole, 2-amino-4-chloro-6-methyl-pyrimidine, 1,3-benzothiazole-2-thiol, 4-amino-N-1,3-thiazol-2-ylbenzenesulfonamide, thiourea, guanidine, 3,4-dimethylpyrazole phosphate, 3,5-dimethylpyrazole, 2,4-diamino-6-trichloromethyl-5-triazine, polyetherionophores, 4-amino-1,2,4-triazole, 3-mercapto-1,2,4-triazole, potassium azide, carbon bisulfide, sodium trithiocarbonate, ammonium dithiocarbamate, 2,3, dihydro-2,2-dimethyl-7-benzofuranol methyl-carbamate, N-(2,6-dimethylphenyl)-N-(methoxyacetyl)-alanine methyl ester, ammonium thiosulfate, 1-hydroxypyrazole, 2-methyl-pyrazole-1-carboxamide, or a combination thereof.

13. The composition prepared by the process of claim 10, wherein the electrophile is formaldehyde, acetaldehyde, propionaldehyde, butyraldehyde, isobutyraldehyde, 2-methyl butanal, 2-ethyl butanal, pentanal, benzaldehyde, furfural, glyoxal, malondialdehyde, succindialdehyde, glutaraldehyde, or a combination thereof.

14. The composition prepared by the process of claim 10, wherein the reaction is carried out at a temperature ranging from about 25° C. to about 40° C.

15. The composition prepared by the process of claim 10, wherein the reaction is carried out at a temperature ranging from about 25° C. to about 50° C.

16. The composition prepared by the process of claim 10, wherein the reaction is carried out at a temperature ranging from about 25° C. to about 60° C.

17. The composition of claim 10, wherein the adduct of Formula A comprises an adduct of the following formula:

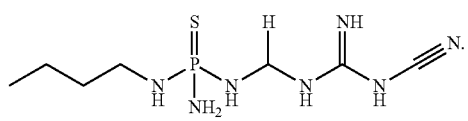

18. The composition of claim 10, wherein the adduct of Formula A comprises an adduct of the following formula:

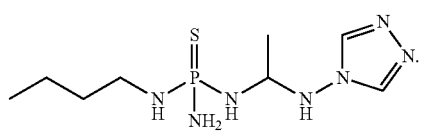

19. A method for preparing a composition comprising:
an adduct of Formula A or Formula B:

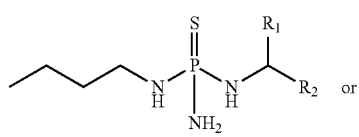

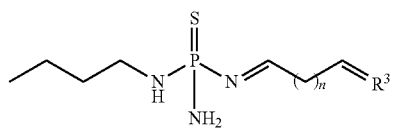

wherein R¹ is H, OH, a substituted or unsubstituted alkyl group, a substituted or unsubstituted alkenyl group, a substituted or unsubstituted alkynyl group, a substituted or unsubstituted heteroalkyl group, a substituted or unsubstituted aryl, or a substituted or unsubstituted heteroaryl;
n is 0, 1, 2, or 3; and
R² and R³ are each independently a nucleophile, which is a nitrification inhibitor, a urease inhibitor, or urea;
free N-(n-butyl)thiophosphoric triamide (NBPT); and
an organic solvent selected from the group consisting of glycols, glycol derivatives, protected glycols, glycol ethers, acetonitrile, DMSO, alkanolamines, alkylsulfones, alkyl amides, monoalcohols, dibasic esters and derivatives thereof, alkylene carbonates, monobasic esters, carboxylic acids, glycol esters, surfactants, and combinations thereof;

the method comprising:
(a) providing a solution of N-(n-butyl)thiophosphoric triamide (NBPT) in the organic solvent, optionally comprising an aqueous solvent;
(b) adding a nucleophile;
(c) adding an electrophile;
(d) reacting the resulting mixture at a temperature ranging from about 25° C. to about 70° C.; and
(e) cooling the mixture to room temperature, wherein the molar ratio of free NBPT:adduct is about 1:1 to about 1:10.

20. The method of claim 19, wherein the organic solvent is an N-alkyl 2-pyrrolidone, glycerol, isopropylidine glycerol, ethyl acetate, acetonitrile, DMSO, propylene glycol, benzyl alcohol, or a combination thereof.

21. The method of claim 19, wherein the nucleophile is urea, N-(n-butyl)thiophosphoric triamide (NBPT), 2-chloro-6-trichloromethyl-pyridine, 5-ethoxy-3-trichloromethyl-1,2,4-thiadiazol, dicyandiamide (DCD), 4-amino-1,2,4-triazole, 3,5-dimethylpyrazole, 2-amino-4-chloro-6-methyl-pyrimidine, 1,3-benzothiazole-2-thiol, 4-amino-N-1,3-thiazol-2-ylbenzenesulfonamide, thiourea, guanidine, 3,4-dimethylpyrazole, 3,5-dimethylpyrazole, 2,4-diamino-6-trichloromethyl-5-triazine, polyetherionophores, 4-amino-1,2,4-triazole, 3-mercapto-1,2,4-triazole, potassium azide, carbon bisulfide, sodium trithiocarbonate, ammonium dithiocarbamate, 2,3, dihydro-2,2-dimethyl-7-benzofuranol methyl-carbamate, N-(2,6-dimethylphenyl)-N-(methoxyacetyl)-alanine methyl ester, ammonium thiosulfate, 1-hydroxypyrazole, 2-methylpyrazole-1-carboxamide, or a combination thereof.

22. The method of claim 19, wherein the electrophile is formaldehyde, acetaldehyde, propionaldehyde, butyraldehyde, isobutyraldehyde, 2-methyl butanal, 2-ethyl butanal, pentanal, benzaldehyde, furfural, glyoxal, malondialdehyde, succindialdehyde, glutaraldehyde, or a combination thereof.

23. The method of claim 19, wherein the reaction is carried out at a temperature ranging from about 25° C. to about 40° C.

24. The method of claim 19, wherein the reaction is carried out at a temperature ranging from about 25° C. to about 50° C.

25. The method of claim 19, wherein the reaction is carried out at a temperature ranging from about 25° C. to about 60° C.

26. The method of claim 19, wherein the adduct of Formula A comprises an adduct of the following formula:

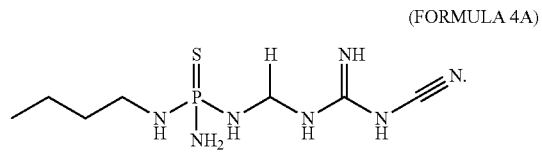 [SMILES: CCCCNP(N)(=S)NCNC(=N)NC#N]

(FORMULA 4A)

27. The method of claim 19, wherein the adduct of Formula A comprises an adduct of the following formula:

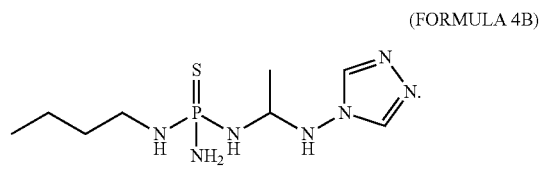 [SMILES: CCCCNP(N)(=S)NC(C)Nn1cnnc1]

(FORMULA 4B)

* * * * *